(12) United States Patent
Hoang

(10) Patent No.: US 10,195,243 B2
(45) Date of Patent: Feb. 5, 2019

(54) PROCESS OF MAKING WINE FROM A WHOLE GRAPE BUNCH, PROCESS OF MAKING POMACE JUICE AND POWDER, AND METHOD OF PRODUCING BEVERAGES ON THE BASIS OF JUICE AND POWDER FROM A GRAPE BUNCH

(71) Applicant: Kieu Hoang, Westlake Village, CA (US)

(72) Inventor: Kieu Hoang, Westlake Village, CA (US)

( * ) Notice: Subject to any disclaimer, the term of this patent is extended or adjusted under 35 U.S.C. 154(b) by 144 days.

(21) Appl. No.: 15/345,721

(22) Filed: Nov. 8, 2016

(65) Prior Publication Data

US 2018/0125917 A1    May 10, 2018
US 2018/0369314 A9    Dec. 27, 2018

Related U.S. Application Data

(63) Continuation of application No. PCT/IB2015/059989, filed on Dec. 24, 2015.

(60) Provisional application No. 62/096,816, filed on Dec. 24, 2014, provisional application No. 62/096,824, filed on Dec. 24, 2014, provisional application No. 62/096,813, filed on Dec. 24, 2014.

(51) Int. Cl.

| | |
|---|---|
| *A61K 36/00* | (2006.01) |
| *A61K 36/87* | (2006.01) |
| *A61K 38/16* | (2006.01) |
| *A61Q 19/08* | (2006.01) |
| *A61K 8/64* | (2006.01) |
| *A61K 9/00* | (2006.01) |
| *C12G 1/02* | (2006.01) |
| *A23L 33/105* | (2016.01) |
| *A23L 33/00* | (2016.01) |
| *A61K 8/9789* | (2017.01) |

(52) U.S. Cl.
CPC ............ *A61K 36/87* (2013.01); *A23L 33/105* (2016.08); *A23L 33/30* (2016.08); *A61K 8/645* (2013.01); *A61K 8/9789* (2017.08); *A61K 9/0095* (2013.01); *A61K 38/168* (2013.01); *A61Q 19/08* (2013.01); *C12G 1/02* (2013.01); *A23V 2002/00* (2013.01); *A61K 2236/15* (2013.01); *A61K 2236/19* (2013.01); *A61K 2236/31* (2013.01); *A61K 2236/53* (2013.01); *A61K 2800/92* (2013.01)

(58) Field of Classification Search
CPC ...................................................... A61K 36/00
USPC ......................................................... 424/725
See application file for complete search history.

(56) References Cited

FOREIGN PATENT DOCUMENTS

KR     2004052398 A   *   6/2004

OTHER PUBLICATIONS

PCT/IB2015/059989 International Preliminary Report on Patentability, dated Jun. 30, 2016.
PCT/IB2015/059989 International Search Report, dated Jun. 30, 2016.

* cited by examiner

*Primary Examiner* — Michael V Meller
(74) *Attorney, Agent, or Firm* — Merek, Blackmon & Voorhees, LLC

(57) ABSTRACT

A food composition for human consumption comprising a plurality of grape ingredients, wherein the plurality of grape ingredients comprise ground flesh, seed, stem, and skin from grapes, and wherein the plurality of grape ingredients further comprise a wine comprising one or more KH Wine proteins. Also, a food composition for human consumption comprising a plurality of pomace ingredients, wherein the plurality of pomace ingredients comprise ground flesh, seed, stem, and skin from pomace in grapes, and wherein the plurality of pomace ingredients further comprise one or more KH Pomace proteins.

Further, a food composition for human consumption comprising a plurality of grape ingredients, wherein the plurality of grape ingredients comprise ground flesh, seed, stem, and skin from grapes, and wherein the plurality of grape ingredients further comprise one or more KH Grape proteins.

8 Claims, 30 Drawing Sheets
(30 of 30 Drawing Sheet(s) Filed in Color)

Figure 22

KIEU HOANG™ AFCC™ WINE INHIBITS THE GROWTH OF CANCER CELLS

KIEU HOANG™ AFCC™ WINE INHIBITS THE GROWTH OF LUNG CANCER CELL

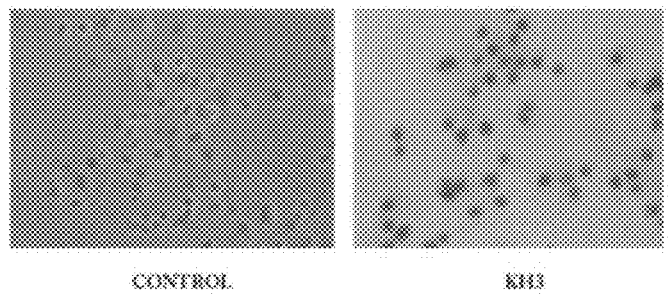

CONTROL　　　　　KH3

KIEU HOANG™ AFCC™ WINE INHIBITS THE GROWTH OF BREAST CANCER CELL

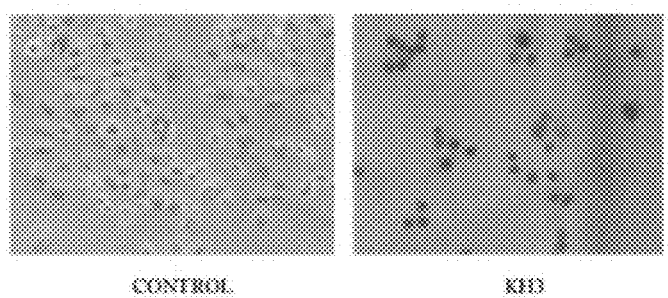

CONTROL　　　　　KH3

*Note: The number of cancer cells mixed with Kieu Hoang ™ red label wine has been reduced significantly as these cancer cells have turned into KH non-cancer good-healthy cells (PATENT NUMBER : 61993164)*

Figure 23

KIEU HOANG™ AFCC™ WINE INHIBITS THE GROWTH OF CANCER CELLS

KIEU HOANG™ AFCC™ WINE INHIBITS THE GROWTH OF LUNG CANCER CELL.

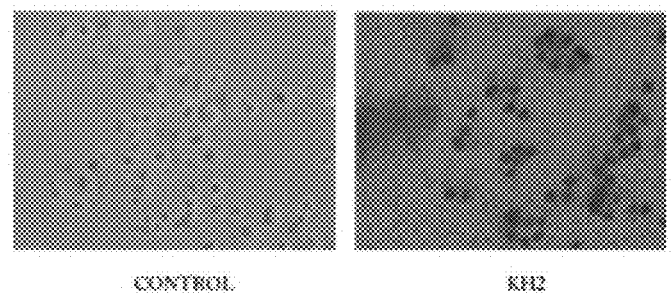

CONTROL      KH2

KIEU HOANG™ AFCC™ WINE INHIBITS THE GROWTH OF BREAST CANCER CELL.

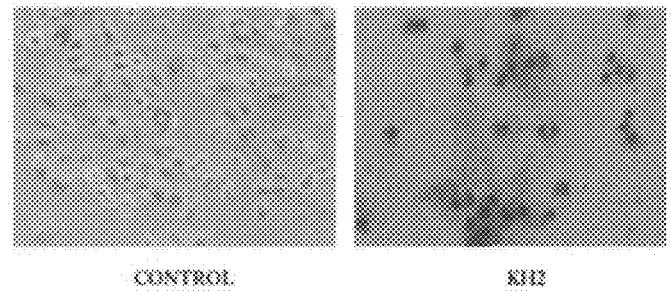

CONTROL      KH2

Note: The number of cancer cells mixed with Kieu Hoang ™ green label wine has been reduced significantly as those cancer cells have turned into KH non-cancer good-healthy cells (picture source: happydna)

Figure 24

KIEU HOANG™ AFCC™ WINE INHIBITS THE GROWTH OF CANCER CELLS

KIEU HOANG™ AFCC™ WINE INHIBITS THE GROWTH OF LUNG CANCER CELL.

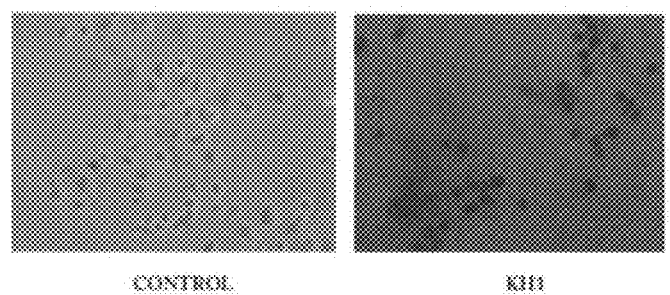

CONTROL        KH

KIEU HOANG™ AFCC™ WINE INHIBITS THE GROWTH OF BREAST CANCER CELL.

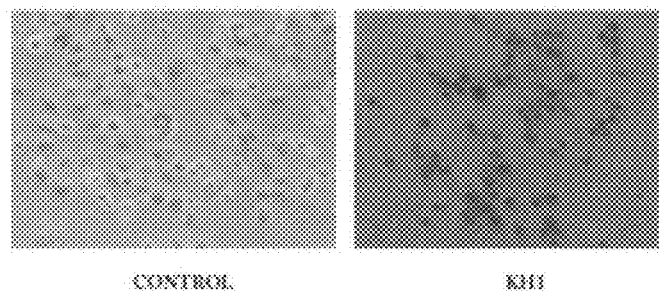

CONTROL        KH

Note: The number of cancer cells mixed with Kieu Hoang ™ blue label wine has been reduced significantly as these cancer cells have turned into KH non-cancer good healthy cells (PATENT NUMBER : 6499746)

GLUCOSE UPTAKE IN KHG(Kiue Hoang Green Label)
KHG Kieu Hoang Green Label helps to generate Insulin for Glucose uptake in DIABETICS
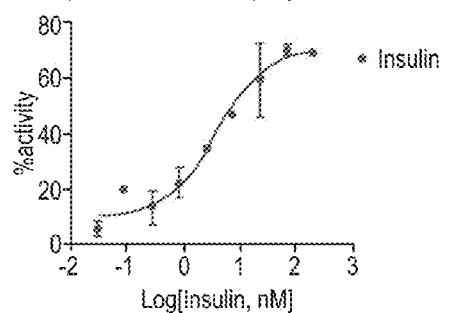
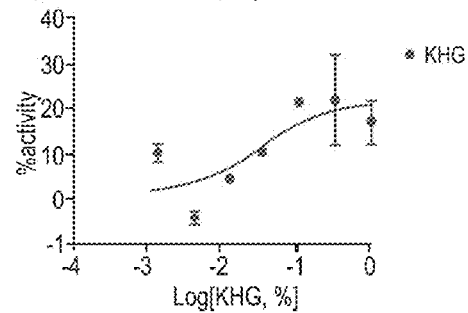
FIG. 27

Figure 39
A
B
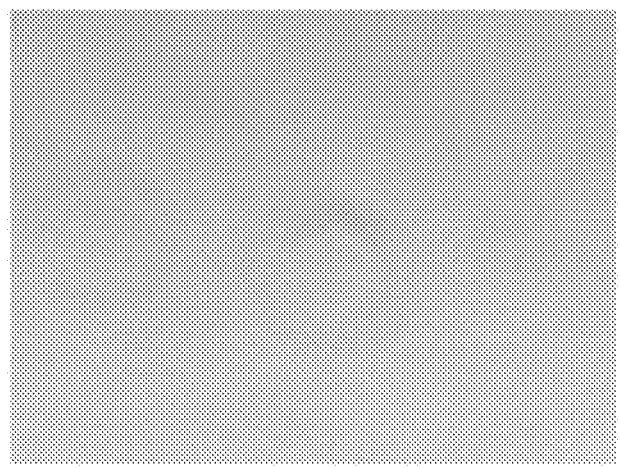
C
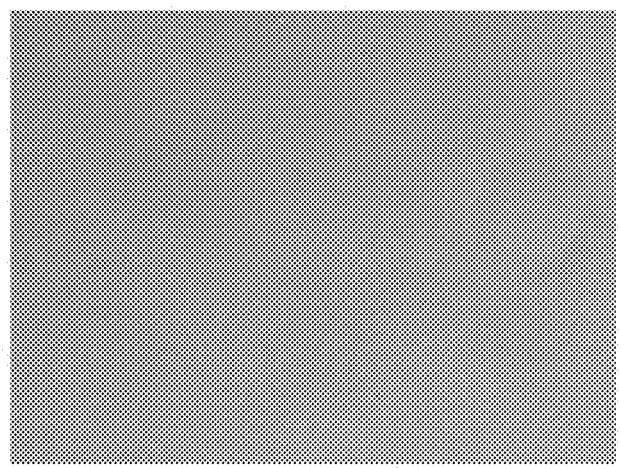

Figure 44
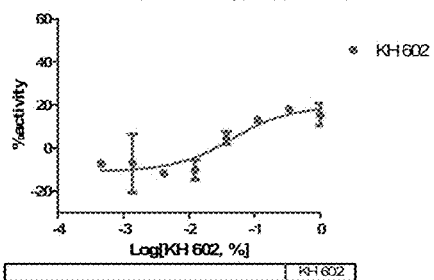
Figure 45
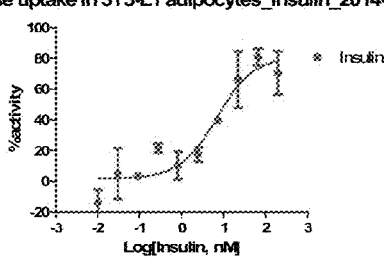 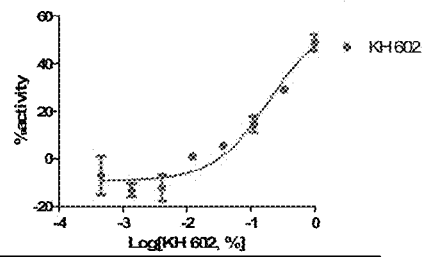

PROCESS OF MAKING WINE FROM A WHOLE GRAPE BUNCH, PROCESS OF MAKING POMACE JUICE AND POWDER, AND METHOD OF PRODUCING BEVERAGES ON THE BASIS OF JUICE AND POWDER FROM A GRAPE BUNCH

RELATED APPLICATIONS

The present patent application claims priority to and is a continuation of Patent Cooperative Treaty ("PCT") application PCT/IB2015/059989, filed Dec. 24, 2015, which claims priority to provisional U.S. Patent Application No. 62/096,813 filed Dec. 24, 2014, provisional U.S. Patent Application No. 62/096,816 filed Dec. 24, 2014, and provisional U.S. Patent Application No. 62/096,824 filed Dec. 24, 2014, which were filed by the inventor hereof. Each of these applications is incorporated by reference herein in their entirety.

TECHNICAL FIELD

The present subject matter relates to a process for producing wine from a grape bunch and further relates to a process for obtaining wine suitable for human consumption from the grape plant, wherein the complete grape bunch is ground and used to make wine. The present subject matter provides a process for obtaining wine from the grape bunch, wherein the skin, seed, flesh and stem are all ground to make wine.

The present subject matter relates to a process for producing beverages on the basis of juice and powder from the pomace and further relates to a process for obtaining fresh juice and powder suitable for human consumption from the pomace plant, wherein the complete pomace is grinded and used to make juice and powder. The present subject matter provides a process for obtaining juice and powder from the pomace, wherein the skin, seed, flesh, and stem of the grape in the pomace are all grinded and centrifuged to make juice and powder.

The present subject matter relates to a process for producing beverages on the basis of juice and powder from the grape bunch and further relates to a process for obtaining fresh juice and powder suitable for human consumption from the grape plant, wherein the complete grape bunch is ground and used to make juice and powder. The present subject matter provides a process for obtaining juice and powder from the grape bunch, wherein the skin, seed, flesh, and stem are all ground and centrifuged to make juice and powder.

BACKGROUND

A grape has 5000 more genes than a human being. Grapes are a popular food staple and have ingredients which are healthy for humans. Wines are popular drinks, with ingredients healthy for humans.

There are presently many wine producers, but these companies create much waste during the production process. In fact, the waste parts of wine processing, such as waste pertaining to the grape skin, stem, or seed, are also useful. The present subject matter describes a process of obtaining wine from a whole grape bunch.

Similarly, pomace is commonly wasted during the production and processing of wine and juice. In fact, the parts of pomace such as skin, stem, or seed are also useful. The present subject matter describes a process of obtaining juice and powder from whole pomace.

Further, there are many grape juice and extraction factories, but the companies create much waste during the production process. In fact, the wasted parts of grapes, such as skin, stem, or seed, are also useful. The present subject matter describes a process of obtaining juice and powder from a whole grape bunch with only minor waste.

SUMMARY

In one embodiment, the present subject matter relates to a food composition for human consumption comprising a plurality of grape ingredients, wherein the plurality of grape ingredients comprises ground flesh, seed, stem, and skin from grapes, and wherein the plurality of grape ingredients further comprise a wine comprising one or more KH Wine proteins.

In this regard, the present subject matter further relates to a method of treating certain disease in a patient comprising administering a food composition for human consumption to a patient in need thereof, the composition comprising a plurality of grape ingredients, wherein the plurality of grape ingredients comprise ground flesh, seed, stem, and skin from grapes, wherein the plurality of grape ingredients further comprise a wine comprising one or more KH Wine proteins such that the composition has a concentration of KH Wine protein above 0%. In one embodiment in this regard, KH Wine healthy cells from the KH Wine proteins, after administration to the patient, send signals to damaged or sick cells, thereby triggering synthesis of proteins to transform the damaged or sick cells to become healthy, wherein the KH Wine healthy cells send signals to other undamaged cells to synthesize proteins to protect the other undamaged cells from damage, infection, and from being prone to DNA and other cellular alterations, and wherein the KH Wine healthy cells send signals to the patient's body to produce new cells that are healthy, thereby preventing the new cells from being affected by intracellular and extracellular damaging signals.

In a further embodiment, the present subject relates to a food composition for human consumption comprising a plurality of pomace ingredients, wherein the plurality of pomace ingredients comprises ground flesh, seed, stem, and skin from pomace in grapes, and wherein the plurality of pomace ingredients further comprise one or more KH Pomace proteins.

In this regard, the present subject matter further relates to a method of treating certain diseases in a patient comprising administering a food composition for human consumption to a patient in need thereof, the composition comprising a plurality of pomace ingredients, wherein the plurality of pomace ingredients comprise ground flesh, seed, stem, and skin from pomace in grapes, wherein the plurality of pomace ingredients further comprise one or more KH Pomace proteins such that the composition has a concentration of KH pomace proteins above 0%. In one embodiment in this regard, KH Pomace healthy cells from the KH Pomace proteins, after administration to the patient, send signals to damaged or sick cells, thereby triggering synthesis of proteins to transform the damaged or sick cells to become healthy, wherein the KH Pomace healthy cells send signals to other undamaged cells to synthesize proteins to protect the other undamaged cells from damage, infection, and from being prone to DNA and other cellular alterations, and wherein the KH Pomace healthy cells send signals to the patient's body to produce new cells that are healthy, thereby preventing the new cells from being affected by intracellular and extracellular damaging signals.

In another embodiment, the present subject matter relates to a food composition for human consumption comprising a plurality of grape ingredients, wherein the plurality of grape ingredients comprises ground flesh, seed, stem, and skin from grapes, and wherein the plurality of grape ingredients further comprise one or more KH Grape proteins.

In this regard, the present subject matter further relates to a method of treating certain diseases in a patient comprising administering a food composition for human consumption to a patient in need thereof, the composition comprising a plurality of grape ingredients, wherein the plurality of grape ingredients comprise ground flesh, seed, stem, and skin from grapes, wherein the plurality of grape ingredients further comprise one or more KH Grape proteins such that the composition has a concentration of KH Grape protein above 0%. In one embodiment in this regard, KH Grape healthy cells from the KH Grape proteins, after administration to the patient, send signals to damaged or sick cells, thereby triggering synthesis of proteins to transform the damaged or sick cells to become healthy, wherein the KH Grape healthy cells send signals to other undamaged cells to synthesize proteins to protect the other undamaged cells from damage, infection, and from being prone to DNA and other cellular alterations, and wherein the KH Grape healthy cells send signals to the patient's body to produce new cells that are healthy, thereby preventing the new cells from being affected by intracellular and extracellular damaging signals.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 22 shows the inhibition of KIEU HOANG™ Red label in lung and breast cancer.

FIG. 23 shows the inhibition of KIEU HOANG™ Green label in lung and breast cancer.

FIG. 24 shows the inhibition of KIEU HOANG™ Blue label in lung and breast cancer.

FIG. 27 shows the Glucose uptake in KIEU HOANG™ Green label, which helps to generate insulin for glucose uptake in diabetics due to the mechanism as described herein.

FIG. 39 shows cells from the inventor (A), from KH103 (B) and from Porcine TB (C).

FIG. 44 shows a graph depicting how KH602 an element in KUNAMIN™, helped to generate insulin for glucose uptakes in Diabetics on Jul. 14, 2014.

FIG. 45 shows a graph depicting KH602 Glucose uptake on Aug. 28, 2014 vs insulin.

DETAILED DESCRIPTION

Unless defined otherwise all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language; however, it will be understood by one of skill in the art, that in some specific instances, an embodiment can alternatively be described using the language "consisting essentially of" or "consisting of."

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

I. Process of Making Wine from a Whole Grape Bunch

An embodiment of the present subject matter is directed to a food composition for human consumption comprising a plurality of grape ingredients, wherein the plurality of grape ingredients comprise ground flesh, seed, stem, and skin from grapes, and wherein the plurality of grape ingredients further comprise one or more KH Wine proteins.

Figure 1:
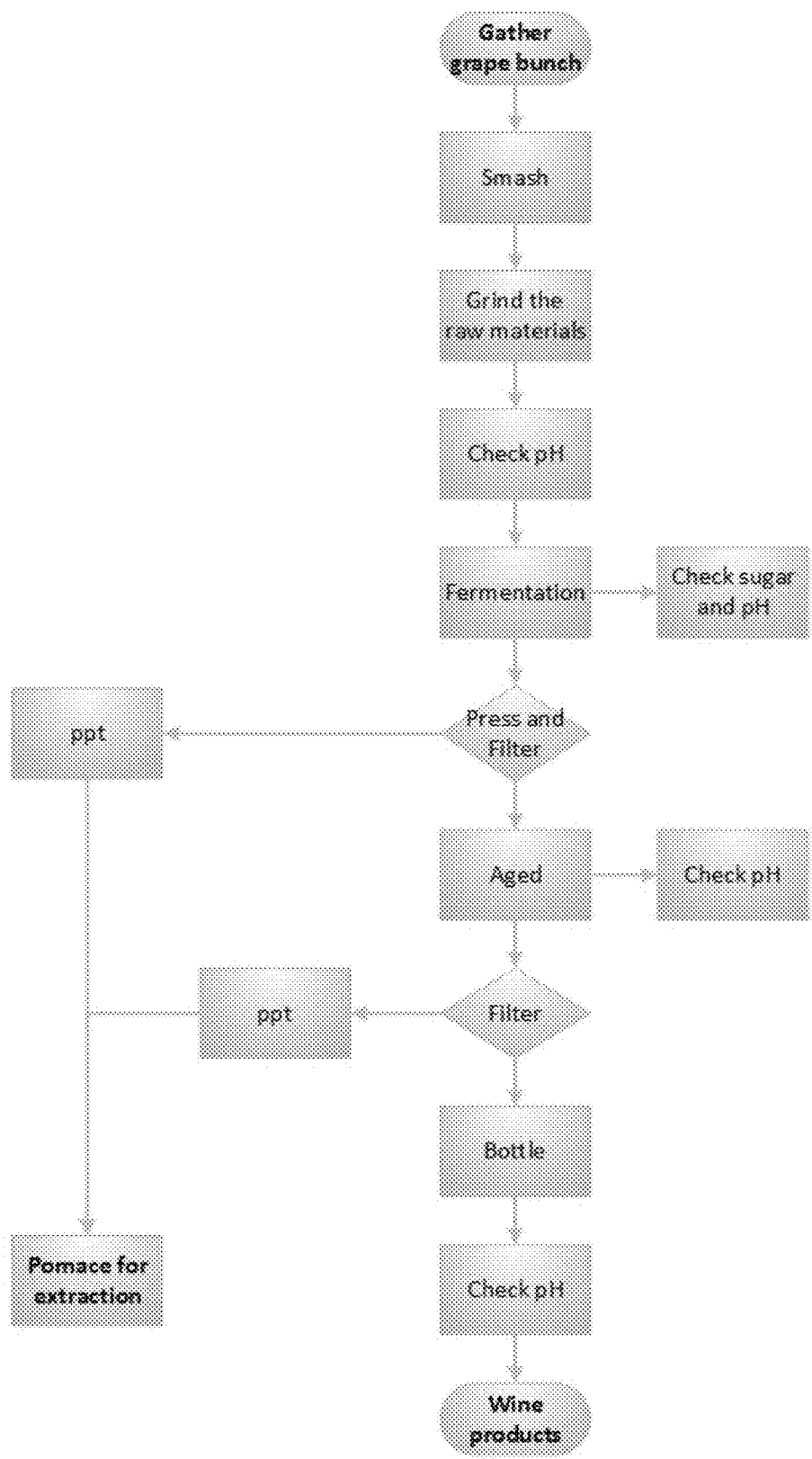
FIG. 1 is a flow chart.

In this regard, the present subject matter describes a method for the production of wine from the grape plant (FIG. 1). The grape bunch is treated immediately after harvest. The whole grape bunch is smashed in a grinder to cut the thick stem at about 20-30° C. All of the raw materials are collected and ground in a superfine mill at about 20-30° C. The raw juice is collected, and the pH of the raw juice is checked, which should be about 3.4-8.0. The raw juice is fermented at about 23-24° C. The pH and sugar are checked during fermentation. The wine is pressed and filtered at room temperature. The precipitate is collected and the wine is transferred.

The wine is aged at about 15-20° C. and the pH is checked during the aging. The wine is filtered at about 15-20° C. The precipitate is collected and the wine in transferred. The wine is bottled and the pH is checked. All of the precipitate is collected for extraction use.

In an embodiment, the wine is spray dryed to create a powder. In an embodiment, a combination of pasteurization and low pH is used for bacterial and viral inactivation. In an embodiment, temperature during manufacturing of the food composition is −10-250° C. In an embodiment, pH during the process is 2.5-10.

In an embodiment, the food composition is KIEU HOANG™ wine containing from a few hundred thousand living cells per ml up to a maximum 5 to 6 billion cells per ml. In an embodiment, the food composition is wine CALIW containing from 500,000-1,000,000 cells per ml. In an embodiment, the food composition is Blue Label wine containing from 10,000,000-50,000,000 cells per ml. In an embodiment, the food composition is Green Label wine containing from 100,000,000 up to 300,000,000 cells per ml. In an embodiment, the food composition is Red Label wine containing from 300,000,000-1,000,000,000 cells per ml. In an embodiment, the food composition is Yellow Label wine containing from 1,100,000,000-2,000,000,000 cells per ml. In an embodiment, the food composition is Pellow Label or Kieu Hoang Proprietary Red Blend wine containing from 2,100,000,000-3,000,000,000 cells per ml. In an embodiment, the food composition is Kogo and Tenno BUDO wine containing from 3,100,000,000-5,000,000,000 cells per ml.

In an embodiment, the composition comprises APOA1 (High Density Lipoprotein) from said KH Wine protein having a molecular weight similar to Human APOA1 (High Density Lipoprotein).

II. Process of Making Pomace Juice and Powder

An embodiment of the present subject matter is directed to a food composition for human consumption comprising a plurality of pomace ingredients, wherein the plurality of pomace ingredients comprise ground flesh, seed, stem, and skin from pomace in grapes, and wherein the plurality of pomace ingredients further comprise one or more KH Pomace proteins.

In an embodiment, the present subject matter describes a method for the production of juice and powder from the pomace plant. The pomace is treated immediately after harvest. The fresh pomace is washed in a cleaning bath at about 0-100° C. The whole pomace is smashed in a grinder to cut the thick stem at about 0-100° C. The raw materials are collected and ground in a superfine mill at about 0-100° C. The raw juice is collected. The pH of the raw juice is checked and should be about 2.5-10. The raw juice is centrifuged at low to high rpm with a normal centrifuge at about −30-30° C. The precipitate and supernatant are collected.

Water at two to four times the volume is added to the precipitate and mixed about 10-100 minutes and centrifuged again at low to high rpm with normal centrifuge at about −30-60° C. The precipitate and supernatant are collected.

Water at one to two times the volume is added, then mixed about 10-100 minutes and centrifuged again at low to high rpm with normal centrifuge at about −30-60° C. The precipitate and supernatant are collected. All the supernatant is mixed for 10-100 minutes at about 0-100° C. The pH of the supernatant is checked and should be about 2.5-10. The supernatant juice is centrifuged at moderate to high rpm with a disc centrifuge at about −30-60° C., and the juice is collected. The juice pH is checked and should be about 2.5-10.

In an embodiment, to make juice product, the collected juice is homogenized at 40-60 MPa. The juice is sterilized at 130-140° C. for 5-20 seconds with a pipe sterilizer. The clear juice is bottled at 25-35° C. The pH of the juice is checked.

In an embodiment, to make a powder product, the collected juice is concentrated in a single-effect falling film evaporator at 65-85° C. until the brix value is 30-50. The concentrated juice is transferred to the centrifugal spray dryer to produce powder.

All precipitate is mixed and capsulized.

In an embodiment, the food composition is a powder, juice, food supplement, or mixed beverage. In an embodiment, the food composition is used in anti-aging cosmetics. In an embodiment, the temperature during manufacturing is −10-250° C. In an embodiment, the pH is 2.5-10. In an embodiment, a combination of pasteurization and dry high temperature heating is used for bacterial and viral inactivation.

In an embodiment, the food composition comprises APOA1 (High Density Lipoprotein) from said KH Pomace proteins having a molecular weight similar to Human APOA1 (High Density Lipoprotein). In an embodiment, the food composition comprises Albumin from said KH Pomace proteins having a molecular weight similar to Human Albumin. In an embodiment, the food composition comprises Alpha 1 Antitrypsin from said KH Pomace proteins having a molecular weight similar to Human Alpha 1 Antitrypsin.

In an embodiment, the KH Pomace protein is KH602. In an embodiment, KH601 and KH602 have the molecular lower band of human immunoglobulin.

III. Method of Producing Beverages on the Basis of Juice and Powder from the Grape Bunch An embodiment of the present subject matter is directed to a food composition for human consumption comprising a plurality of grape ingredients, wherein the plurality of grape ingredients comprise ground flesh, seed, stem, and skin from grapes, and wherein the plurality of pomace ingredients further comprise one or more KH Grape proteins.

In an embodiment, the food composition is a powder, juice, food supplement, or mixed beverage. In an embodiment, the temperature during manufacturing is −10-250° C. In an embodiment, the pH is 2.5-10. In an embodiment, a combination of pasteurization and dry high temperature heating is used for bacterial and viral inactivation.

In an embodiment, the food composition comprises APOA1 (High Density Lipoprotein) from said KH Grape proteins having a molecular weight similar to Human APOA1 (High Density Lipoprotein). In an embodiment, the food composition comprises Albumin from said KH Grape proteins having a molecular weight similar to Human Albumin. In an embodiment, the food composition comprises Alpha 1 Antitrypsin from said KH Grape proteins having a molecular weight similar to Human Alpha 1 Antitrypsin. In an embodiment, the food composition comprises immunoglobulin and APOA-1 from said KH Grape proteins having a molecular weight similar to Human immunoglobulin and APOA-1.

In an embodiment, the KH Grape protein is KH602. In an embodiment, the KH Grape protein is KHJ.

Figure 40:
FIG. 40 shows a grape process flow chart.

In an embodiment, the present subject matter describes a method for the production of juice and powder from the grape plant (FIG. 40). The grape bunch is treated immediately after harvest. The fresh grape bunch is washed in a cleaning bath at about 0-100° C. The whole grape bunch is smashed in a grinder to cut the thick stem at about 0-100° C. All of the raw materials are collected and ground in a superfine mill at about 0-100° C. The raw juice is collected, and the pH of the raw juice is checked, which should be about 2.5-10. The raw juice is centrifuged at low to high rpm with normal centrifuge at about −30-30° C. The precipitate and supernatant are collected.

Water at two to four times the volume is added to the precipitate and mixed about 10-100 minutes and centrifuged again at low to high rpm with normal centrifuge at about −30-60° C. The precipitate and supernatant are collected.

Water at one to two times the volume is added, then mixed about 10-100 minutes and centrifuged again at low to high rpm with normal centrifuge at about −30-60° C. The precipitate and supernatant are collected. All the supernatant is mixed for 10-100 minutes at about 0-100° C. The pH of the supernatant is checked and should be about 2.5 to 10. The supernatant juice is centrifuged at moderate to high rpm with a disc centrifuge at about −30-60° C., and the juice is collected. The juice pH is checked and should be about 2.5-10.

In an embodiment, to make a juice product, the collected juice is homogenized at 40-60 MPa. The juice is sterilized at 130-140° C. for 5-20 seconds with a pipe sterilizer. The clear juice is bottled at 25-35° C. The pH of the juice is checked.

In an embodiment, to make a powder product, the collected juice is concentrated in a single-effect falling film evaporator at 65-85° C. until the brix value is 30-50. The concentrated juice is transferred to the centrifugal spray dryer to produce powder.

All precipitate is mixed and capsulized.

IV. Methods of Treatment/Prevention

An embodiment of the present subject matter is directed to a method of treating certain diseases in a patient comprising administering the food composition to a patient in need thereof, wherein the food composition has a concentration of KH Wine protein above 0%.

Another embodiment of the present subject matter is directed to a method of treating certain diseases in a patient comprising administering the food composition to a patient in need thereof, wherein the food composition has a concentration of KH Pomace proteins above 0%.

A further embodiment of the present subject matter is directed to a method of treating certain diseases in a patient comprising administering the food composition to a patient in need thereof, wherein the food composition has a concentration of KH Grape proteins above 0%.

In an embodiment, administration of the food composition lowers triglycerides and cholesterol and increases High Density Lipoprotein (APOA1) in the patient. In an embodiment, administration of the food composition increases glucose uptake in the patient. In an embodiment, administration of the food composition cleans plaque and provides heart, brain, and artery blockage protection in the patient. In another embodiment, administration of the food composition treats and/or prevents diabetes in a patient. In a still further embodiment, administration of the food compositions treats and/or prevents hypercholesterolemia and/or hyperlipidemia in a patient.

In an embodiment, administration of the food composition inhibits growth of various cancer cells in the patient. Exemplary in this regard, the food composition described herein inhibits growth of leukemia cells in a patient, treats leukemia in a patient, and/or prevents leukemia in a patient. In an embodiment, administration of the food composition prevents the development of leukemia in mice after two times of implantation with a total of 30,000,000 Leukemia cancer cells through vein injection (first time with 10,000,000 cells and second time with 20,000,000 cells for those mice that did not develop leukemia after the first implantation). Similarly, the food composition described herein inhibits the growth of breast and/or lung cancer cells in a patient, treats breast and/or lung cancer in a patient, and/or prevents breast and/or lung cancer in a patient.

In an embodiment, administration of the food composition suppresses inflammation in the patient due to different causes of disease.

EXAMPLES

In Vitro Study 1—Lipid Panel

Figure 2:
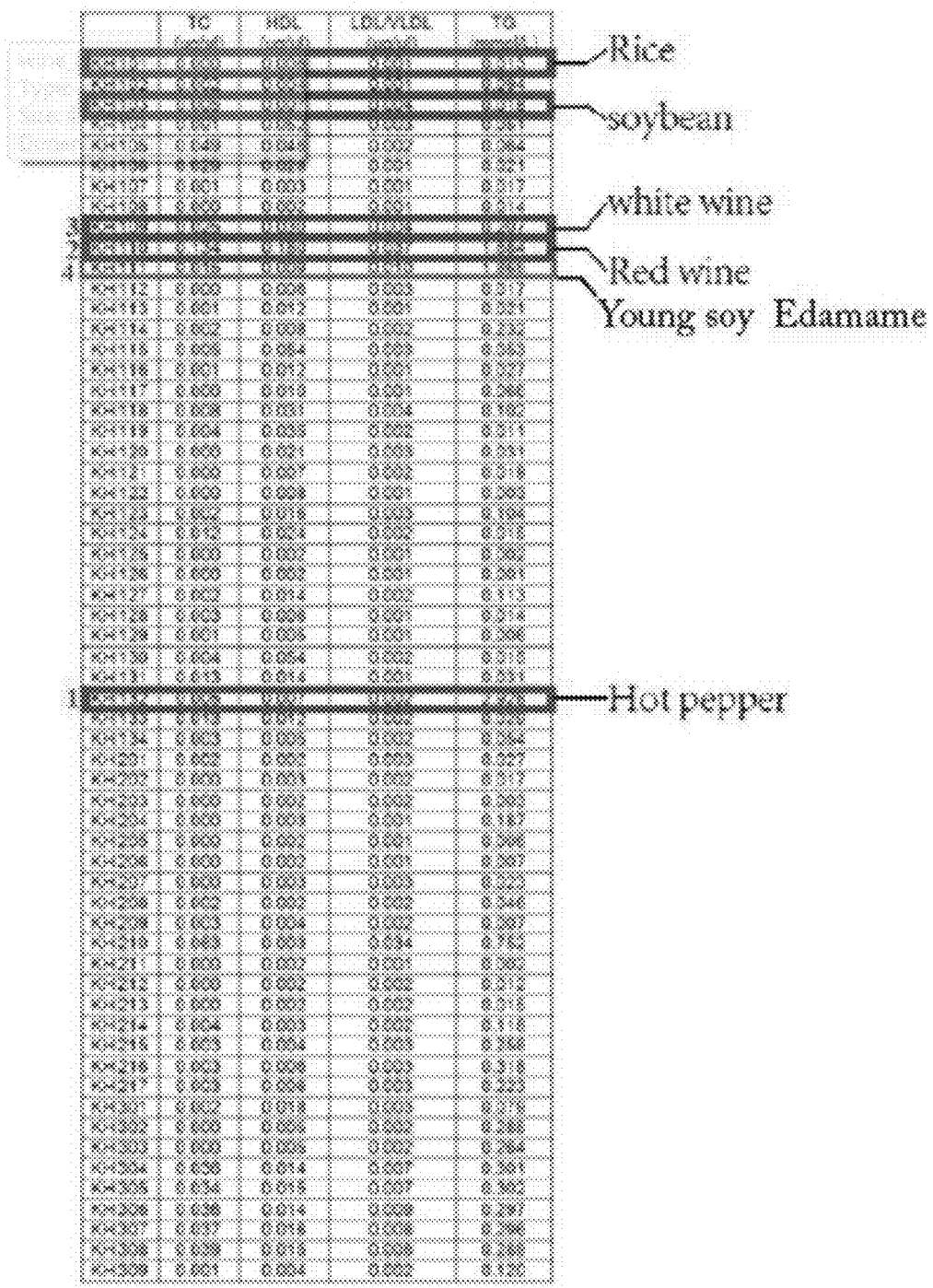
FIG. 2 is a chart of wine tested items.

The highest level of HDL among 100 tested items was found in KIEU HOANG™ wine. FIG. 2 is a chart of wine tested items. KIEU HOANG™ wine red and white without specific number of cells in them were tested. The red wine KH110 contains the highest level of HDL with 0.180/uL. Tests were performed by one of the top ten CRO labs in the world.

The objective of this study was to quantify Cholesterol/Cholesteryl Ester (TC), HDL Cholesterol (HDLC), LDL/VLDL Cholesterol (LDLC/VLDLC), and Triglyceride (TG) concentration in RAAS products.

The Cholesterol/Cholesteryl Ester Quantitation Kit provides a simple method for sensitive quantification of free cholesterol, cholesteryl esters, or both by colorimetric or fluorometric methods. The majority of the cholesterol in blood is in the form of cholesteryl esters which can be hydrolyzed to cholesterol by cholesterol esterase. Cholesterol is then oxidized by cholesterol oxidase to yield $H_2O_2$ which reacts with a sensitive cholesterol probe to produce color ($\lambda$max=570 nm) and fluorescence (Ex/Em=535/590 nm). The assay detects total cholesterol (cholesterol and cholesteryl esters) in the presence of cholesterol esterase or free cholesterol in the absence of cholesterol esterase in the reaction.

BioVision's HDL and LDL/VLDL Cholesterol Quantification Kit provides a simple quantification method of HDL and LDL/VLDL after a convenient separation of HDL from LDL and VLDL (very low-density lipoprotein) in serum samples. In the assay, cholesterol oxidase specifically recognizes free cholesterol and produces products which react with probe to generate color ($\lambda$=570 nm) and fluorescence (Ex/Em=538/587 nm). Cholesterol esterase hydrolyzes cholesteryl ester into free cholesterol, therefore, cholesterol ester and free cholesterol can be detected separately in the presence and absence of cholesterol esterase in the reactions.

Likewise, the Triglyceride Quantification Kit provides a sensitive, easy assay to measure triglyceride concentration in variety of samples. In the assay, triglycerides are converted to free fatty acids and glycerol. The glycerol is then oxidized to generate a product which reacts with the probe to generate colorimetric (spectrophotometry at $\lambda$=570 nm) and fluorometric (Ex/Em=535/590 nm) methods. The kit can detect 1 pmol-10 nmol (or 1~10000 µM range) of triglyceride in various samples listed below in Table 1:

TABLE 1

|  | Volume | Sample | Storage |
| --- | --- | --- | --- |
| KH 101 | ~1 ml | use as supplied | −20° C. |
| KH 102 | ~1 ml | use as supplied | −20° C. |

TABLE 1-continued

|  | Volume | Sample | Storage |
| --- | --- | --- | --- |
| KH 103 | ~1 ml | use as supplied | −20° C. |
| KH 104 | ~1 ml | use as supplied | −20° C. |
| KH 105 | ~1 ml | use as supplied | −20° C. |
| KH 106 | ~1 ml | use as supplied | −20° C. |
| KH 107 | ~1 ml | use as supplied | −20° C. |
| KH 108 | ~1 ml | use as supplied | −20° C. |
| KH 109 | ~1 ml | use as supplied | −20° C. |
| KH 110 | ~1 ml | use as supplied | −20° C. |
| KH 111 | ~1 ml | use as supplied | −20° C. |
| KH 112 | ~1 ml | use as supplied | −20° C. |
| KH 113 | ~1 ml | use as supplied | −20° C. |
| KH 114 | ~1 ml | use as supplied | −20° C. |
| KH 115 | ~1 ml | use as supplied | −20° C. |
| KH 116 | ~1 ml | use as supplied | −20° C. |
| KH 117 | ~1 ml | use as supplied | −20° C. |
| KH 118 | ~1 ml | use as supplied | −20° C. |
| KH 119 | ~1 ml | use as supplied | −20° C. |
| KH 120 | ~1 ml | use as supplied | −20° C. |
| KH 121 | ~1 ml | use as supplied | −20° C. |
| KH 122 | ~1 ml | use as supplied | −20° C. |
| KH 123 | ~1 ml | use as supplied | −20° C. |
| KH 124 | ~1 ml | use as supplied | −20° C. |
| KH 125 | ~1 ml | use as supplied | −20° C. |
| KH 126 | ~1 ml | use as supplied | −20° C. |
| KH 127 | ~1 ml | use as supplied | −20° C. |
| KH 128 | ~1 ml | use as supplied | −20° C. |
| KH 129 | ~1 ml | use as supplied | −20° C. |
| KH 130 | ~1 ml | use as supplied | −20° C. |
| KH 131 | ~1 ml | use as supplied | −20° C. |
| KH 132 | ~1 ml | use as supplied | −20° C. |
| KH 133 | ~1 ml | use as supplied | −20° C. |
| KH 134 | ~1 ml | use as supplied | −20° C. |
| KH 201 | ~1 ml | use as supplied | −20° C. |
| KH 202 | ~1 ml | use as supplied | −20° C. |
| KH 203 | ~1 ml | use as supplied | −20° C. |
| KH 204 | ~1 ml | use as supplied | −20° C. |
| KH 205 | ~1 ml | use as supplied | −20° C. |
| KH 206 | ~1 ml | use as supplied | −20° C. |
| KH 208 | ~1 ml | use as supplied | −20° C. |
| KH 209 | ~1 ml | use as supplied | −20° C. |
| KH 210 | ~1 ml | use as supplied | −20° C. |
| KH 211 | ~1 ml | use as supplied | −20° C. |
| KH 212 | ~1 ml | use as supplied | −20° C. |
| KH 213 | ~1 ml | use as supplied | −20° C. |
| KH 214 | ~1 ml | use as supplied | −20° C. |
| KH 215 | ~1 ml | use as supplied | −20° C. |
| KH 216 | ~1 ml | use as supplied | −20° C. |
| KH 217 | ~1 ml | use as supplied | −20° C. |
| KH 301 | ~1 ml | use as supplied | −20° C. |
| KH 302 | ~1 ml | use as supplied | −20° C. |
| KH 303 | ~1 ml | use as supplied | −20° C. |
| KH 304 | ~1 ml | use as supplied | −20° C. |
| KH 305 | ~1 ml | use as supplied | −20° C. |
| KH 306 | ~1 ml | use as supplied | −20° C. |
| KH 307 | ~1 ml | use as supplied | −20° C. |
| KH 308 | ~1 ml | use as supplied | −20° C. |
| KH 309 | ~1 ml | use as supplied | −20° C. |

Total Cholesterol/Cholesteryl Ester Quantification by Fluorometric Method (TC)

Cholesterol/Cholesteryl Ester Quantitation Kit (Catalog #K603-100; 100 assays; Store at −20° C.).

The Kit Contents are as listed below in Table 2:

TABLE 2

| Components | K622-100 | Cap Code | Part Number |
| --- | --- | --- | --- |
| Cholesterol Assay Buffer | 25 ml | WM | K603-100-1 |
| Cholesterol Probe (in DMSO, anhydrous) | 200 µl | Red | K603-100-2A |

TABLE 2-continued

| Components | K622-100 | Cap Code | Part Number |
|---|---|---|---|
| Enzyme Mix (lyophilized) | 1 vial | Green | K603-100-4 |
| Cholesterol Esterase (lyophilized) | 1 vial | Blue | K603-100-5 |
| Cholesterol Standard (2 µg/µl) | 100 µl | Yellow | K603-100-6 |

Store kit at −20° C. and protect from light. Warm to room temperature before use. Keep enzymes and cholesterol standard on ice while using.

Warm the Cholesterol Probe to room temperature to thaw the DMSO solution before use. Store at −20° C., protect from light.

Dissolve the Cholesterol Esterase in 220 µl Cholesterol Assay Buffer before use. Aliquot and store at −20° C.

Dissolve the Enzyme Mix in 220 µl Cholesterol Assay Buffer before use. Aliquot and store at −20° C.

Standard Curve Preparation:

Dilute the Cholesterol Standard to 25 ng/µl by adding 10 µl of the Cholesterol Standard to 790 µl of Cholesterol Assay Buffer, mix well. Add 0, 4, 8, 12, 16, 20 µl into a series of wells. Adjust volume to 50 l/well with Cholesterol Assay Buffer to generate 0, 0.1, 0.2, 0.3, 0.4, 0.5 µg/well of the Cholesterol Standard.

Sample Preparation:

Add 5 µl test samples in a 96-well clear bottom black plate, Adjust to the final volume of 50 µl/well with Cholesterol Assay Buffer.

Mix enough reagents for the number of samples and standards to be performed. For each well, prepare a total 50 µl Reaction Mix:

45.6 µl Cholesterol Assay Buffer
0.4 µl Cholesterol Probe
2 µl Cholesterol Enzyme Mix
2 µl Cholesterol Esterase Mix well Add 50 µl of the Reaction Mix to each well containing standard or test samples.

Incubate the reaction for 60 minutes at 37° C., protect from light.

Measure fluorescence at Ex/Em 535/590 nm in ENSPIRE.

Calculations:

Subtract 0 standard reading from readings. Plot the standard curve. Apply the sample readings to the standard curve to determine sample cholesterol amount in the reaction well.

Sample Cholesterol Concentrations:

$$C = A/V \ (\mu g/\mu l)$$

Where: A is the sample cholesterol amount from the standard curve (µg).

V is original sample volume added to the sample reaction well (µl).

HDL and LDL/VLDL Cholesterol Quantification by Fluorometric Method (HDLC and LDLC/VLDLC)

HDL and LDL&VLDL Cholesterol Quantification Kit (Catalog #K613-100; 100 assays; Store at −20° C.). The Kit Contents are as follows in Table 3:

TABLE 3

| Components | Volume | Cap Code | Part No. |
|---|---|---|---|
| Cholesterol Assay Buffer | 25 ml | WM | K613-100-1 |
| 2X LDL/VLDL Precipitation Buffer | 10 ml | NM | K613-100-2 |
| Cholesterol Probe (in DMSO, anhydrous) | 200 µl | Red | K613-100-3A |

TABLE 3-continued

| Components | Volume | Cap Code | Part No. |
|---|---|---|---|
| Enzyme Mix (Lyophilized) | 1 vial | Green | K613-100-5 |
| Cholesterol Esterase (Lyophilized) | 1 vial | Blue | K613-100-6 |
| Cholesterol Standard (2 µg/µl) | 100 µl | Yellow | K613-100-7 |

Warm the Cholesterol Probe to room temperature, store at −20° C., protect from light.

Dissolve the Cholesterol Esterase in 220 µl Cholesterol Assay Buffer. Aliquot and store at −20° C.

Dissolve the Enzyme Mix in 220 µl Cholesterol Assay Buffer prior to use. Aliquot and store at −20° C.

Separation of HDL and LDL/VLDL:

Mix 100 µl of 2× Precipitation Buffer with 100 µl of serum sample in microcentrifuge tubes. Incubate 10 min at RT, centrifuge at 2000×g (5000 rpm) for 10 min. Transfer the supernatant (HDL) into new labeled tubes. Spin the precipitates (LDL/VLDL) again, Remove HDL supernatant. Resuspend the precipitate in 200 µl PBS.

Note A: If the supernatant is cloudy, the sample should be re-centrifuged. If the sample remains cloudy, dilute the sample 1:1 with PBS, and repeat the separation procedure. Multiply final results by two (2) due to the dilution with the 2× Precipitation Buffer.

Standard Curve and Sample Preparations:

Dilute the Cholesterol Standard to 25 ng/µl by adding 10 µl of the Cholesterol Standard to 790 µl of Cholesterol Assay Buffer, Add 0, 4, 8, 12, 16, 20 µl into a series of wells in a 96-well clear bottom black plate. Adjust volume to 50 µl/well with Cholesterol Assay Buffer to generate 0, 0.1, 0.2, 0.3, 0.4, 0.5 µg/well of the Cholesterol Standard. Use 5 µl of the HDL or LDL/VLDL fraction, adjust the total volume to 50 µl/well with Cholesterol Assay Buffer.

Mix enough reagents for the number of assays performed. For each assay, prepare a total 50 µl Reaction Mix containing:

45.6 µl Cholesterol Assay Buffer
0.4 µl Cholesterol Probe
2 µl Enzyme Mix
2 µl Cholesterol Esterase Add 50 µl of the Reaction Mix to each well containing the Cholesterol Standard or test samples, mix well. Incubate the reaction for 60 minutes at 37° C., protect from light. Measure fluorescence at Ex/Em 538/587 nm in ENSPIRE.

Calculations:

Subtract 0 standard reading from readings. Plot the standard curve. Apply the sample readings to the standard curve to determine sample cholesterol amount in the reaction well.

Sample Cholesterol Concentrations:

$$C = A/V \ (\mu g/\mu l)$$

Where: A is the sample cholesterol amount from the standard curve (µg).

V is original sample volume added to the sample reaction well (µl).

Triglyceride Quantification by Fluorometric Method (TG)

Triglyceride Quantification Kit (Catalog #K622-100; 100 assays; Store at −20° C.). The Kit Contents are as follows in Table 4:

TABLE 4

| Components | K622-100 | Cap Code | Part Number |
|---|---|---|---|
| Triglyceride Assay Buffer | 25 ml | WM | K622-100-1 |
| Triglyceride Probe (lyophilized) | 1 vial | Red | K622-100-2 |

TABLE 4-continued

| Components | K622-100 | Cap Code | Part Number |
|---|---|---|---|
| Dimethylsulfoxide (DMSO, Anhydrous) | 0.4 ml | Brown | K622-100-3 |
| Lipase | 0.5 ml | Blue | K622-100-4 |
| Triglyceride Enzyme Mix (lyophilized) | 1 vial | Green | K622-100-5 |
| Triglyceride Standard (1 mM) | 0.2 ml | Yellow | K622-100-6 |

Store kit at −20° C., protect from light. Warm Triglyceride Assay Buffer to room temperature before use. Briefly centrifuge all small vials prior to opening.

Dissolve the Triglyceride Probe in 220 µl anhydrous DMSO (provided) before use. Store at −20° C., protect from light and moisture.

Dissolve the Triglyceride Enzyme Mix in 220 µl Triglyceride Assay Buffer. Aliquot and store at −20° C.

Dissolve the Lipase in 220 µl Triglyceride Assay Buffer. Aliquot and store at −20° C.

Standard Curve Preparation:

Re-dissolve in hot water bath (80~100° C.) for 1 minute or until the standard looks cloudy, vortex for 30 seconds, repeat the heat and vortex one more time. Dilute the Triglyceride Standard to 0.01 mM with the Triglyceride Assay Buffer. Add 0, 10, 20, 30, 40, 50 µl into each well individually. Adjust volume to 50 µl/well with Triglyceride Assay Buffer to generate 0.1, 0.2, 0.3, 0.4, 0.5 nmol/well of Triglyceride Standard.

Sample Preparation:

Add 5 µl test samples in a 96-well clear bottom black plate, Adjust to the final volume of 50 l/well with Triglyceride Assay Buffer.

Add 2 µl of lipase to each standard and sample well. Mix and incubate 20 min at RT to convert triglyceride to glycerol and fatty acid.

For the Triglyceride Reaction Mix: mix enough reagents for the number of samples and standards to be performed. For each well, prepare a total 50 µl Reaction Mix:

47.6 µl Triglyceride Assay Buffer 0.4 µl Triglyceride Probe

2 µl Triglyceride Enzyme Mix

Add 50 µl of the Reaction Mix to each well containing the Triglyceride Standard, test samples and controls. Mix well. Incubate at room temperature for 30 minutes, protect from light.

Measure fluorescence at Ex/Em 535/590 nm in ENSPIRE.

Calculations:

Correct background by subtracting the value derived from the 0 triglyceride standard from all sample readings. Plot the standard curve. Apply sample Readings to the standard curve.

Triglyceride Concentration can then be Calculated:

$$C = Ts/Sv \text{ (nmol/µl or µmol/ml or mM)}$$

Where: Ts is triglyceride amount from standard curve (nmol).

Sv is the sample volume (before dilution) added in sample wells (µl).

Results

TABLE 5

Figure 3:
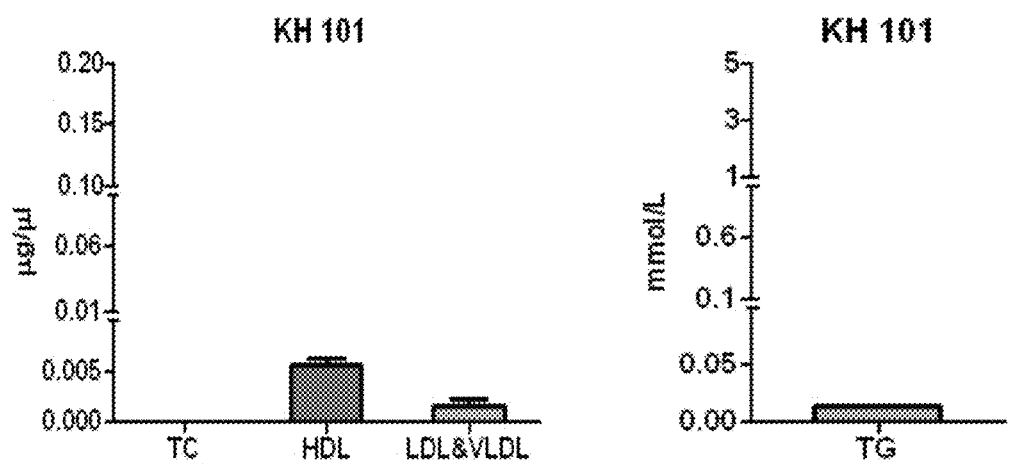
FIG. 3 shows the quantification of TC, HDL, LDL/VLDL and TG of sample KH 101.

Quantification of TC, HDL, LDL/VLDL and TG of sample KH 101 (FIG. 3)

| Sample | TC (µg/µl) | HDL (µg/µl) | LDL/VLDL (µg/µl) | TG (mmol/L) |
|---|---|---|---|---|
| KH 101 | 0.000 ± 0.000 | 0.006 ± 0.000 | 0.001 ± 0.000 | 0.013 ± 0.000 |

TABLE 6

Figure 4:
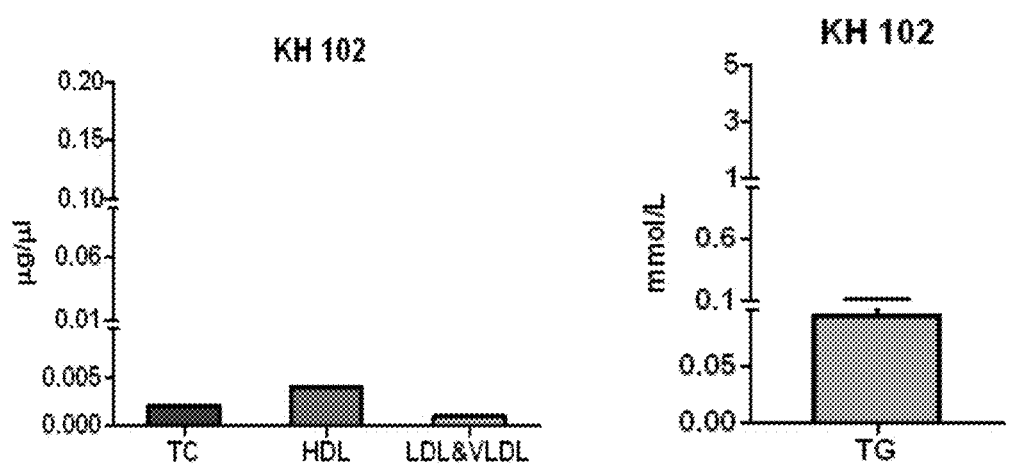
FIG. 4 shows the quantification of TC, HDL, LDL/VLDL and TG of sample KH 102.

Quantification of TC, HDL, LDL/VLDL and TG of sample KH102 (FIG. 4)

| Sample | TC (µg/µl) | HDL (µg/µl) | LDL/VLDL (µg/µl) | TG (mmol/L) |
|---|---|---|---|---|
| KH 102 | 0.002 ± 0.000 | 0.004 ± 0.000 | 0.001 ± 0.000 | 0.094 ± 0.011 |

TABLE 7

Figure 5:
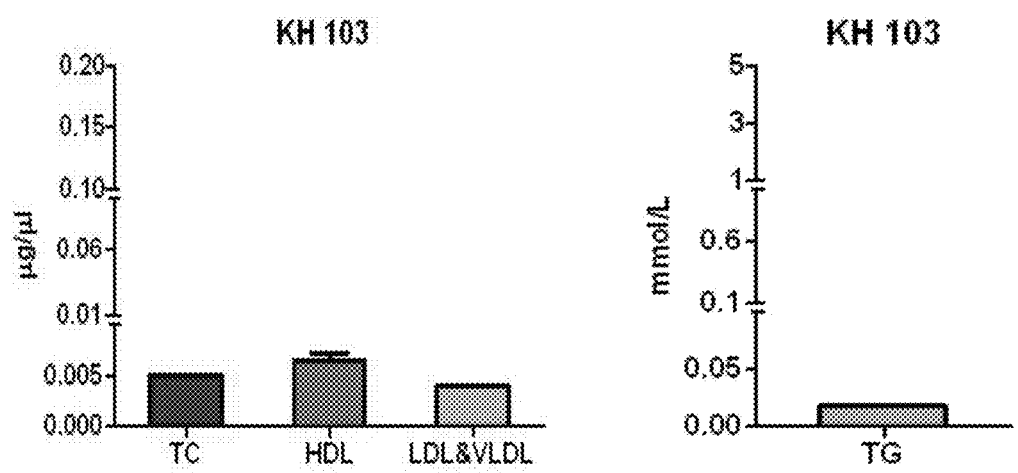
FIG. 5 shows the quantification of TC, HDL, LDL/VLDL and TG of sample KH 103.

Quantification of TC, HDL, LDL/VLDL and TG of sample KH 103 (FIG. 5)

| Sample | TC (µg/µl) | HDL (µg/µl) | LDL/VLDL (µg/µl) | TG (mmol/L) |
|---|---|---|---|---|
| KH 103 | 0.005 ± 0.000 | 0.007 ± 0.000 | 0.004 ± 0.000 | 0.018 ± 0.000 |

TABLE 8

Figure 6:
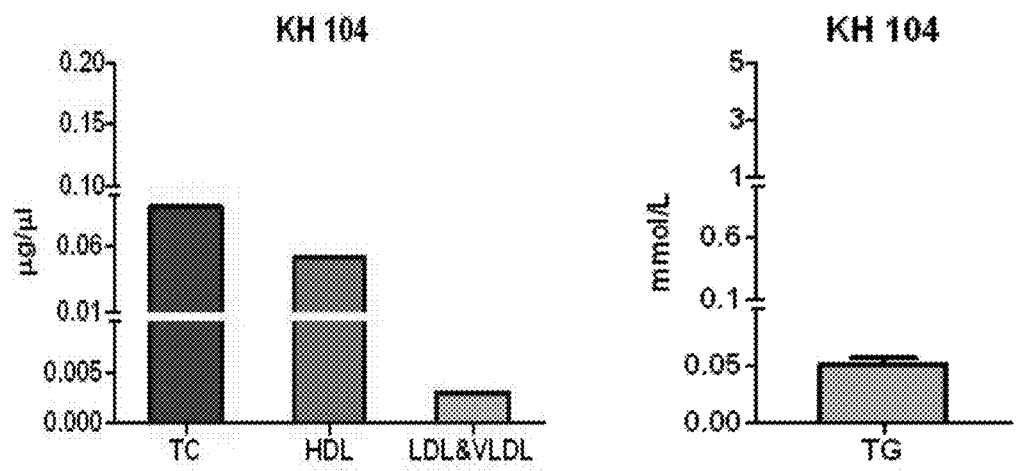
FIG. 6 shows the quantification of TC, HDL, LDL/VLDL and TG of sample KH 104.

Quantification of TC, HDL, LDL/VLDL and TG of sample KH 104 (FIG. 6)

| Sample | TC (µg/µl) | HDL (µg/µl) | LDL/VLDL (µg/µl) | TG (mmol/L) |
|---|---|---|---|---|
| KH 104 | 0.091 ± 0.000 | 0.052 ± 0.001 | 0.003 ± 0.000 | 0.051 ± 0.006 |

TABLE 9

Figure 7:
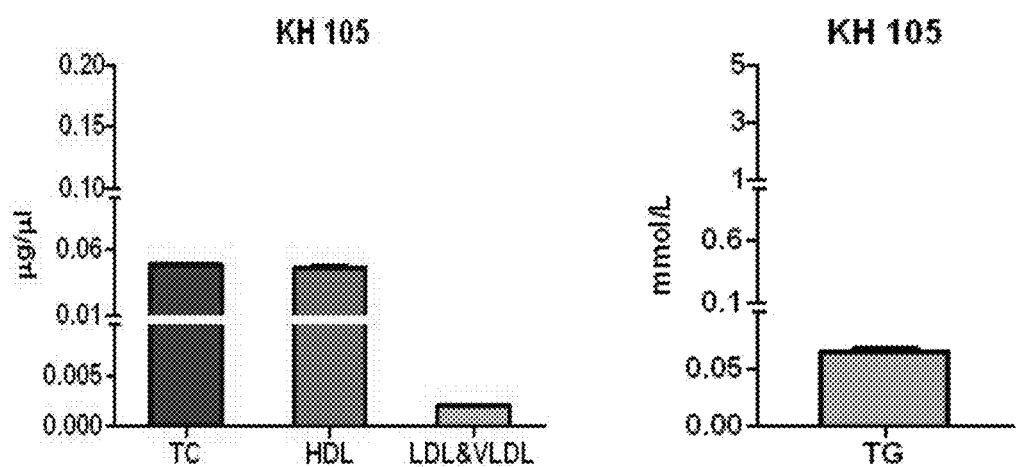
FIG. 7 shows the quantification of TC, HDL, LDL/VLDL and TG of sample KH 105.

Quantification of TC, HDL, LDL/VLDL and TG of sample KH 105 (FIG. 7)

| Sample | TC (µg/µl) | HDL (µg/µl) | LDL/VLDL (µg/µl) | TG (mmol/L) |
|---|---|---|---|---|
| KH 105 | 0.049 ± 0.001 | 0.046 ± 0.001 | 0.002 ± 0.000 | 0.064 ± 0.004 |

TABLE 10

Figure 8:
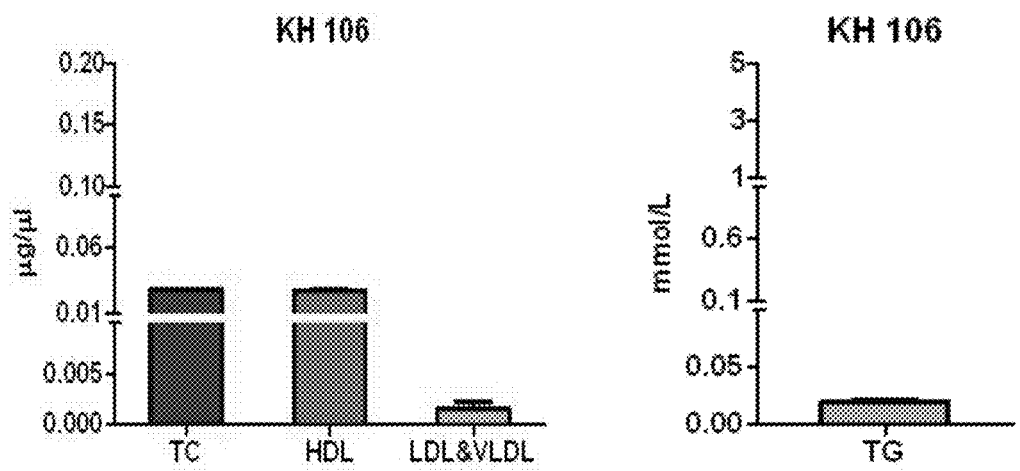
FIG. 8 shows the quantification of TC, HDL, LDL/VLDL and TG of sample KH106.

Quantification of TC, HDL, LDL/VLDL and TG of sample KH 106 (FIG. 8)

| Sample | TC (µg/µl) | HDL (µg/µl) | LDL/VLDL (µg/µl) | TG (mmol/L) |
|---|---|---|---|---|
| KH 106 | 0.029 ± 0.000 | 0.028 ± 0.001 | 0.001 ± 0.000 | 0.021 ± 0.000 |

TABLE 11

Figure 9:
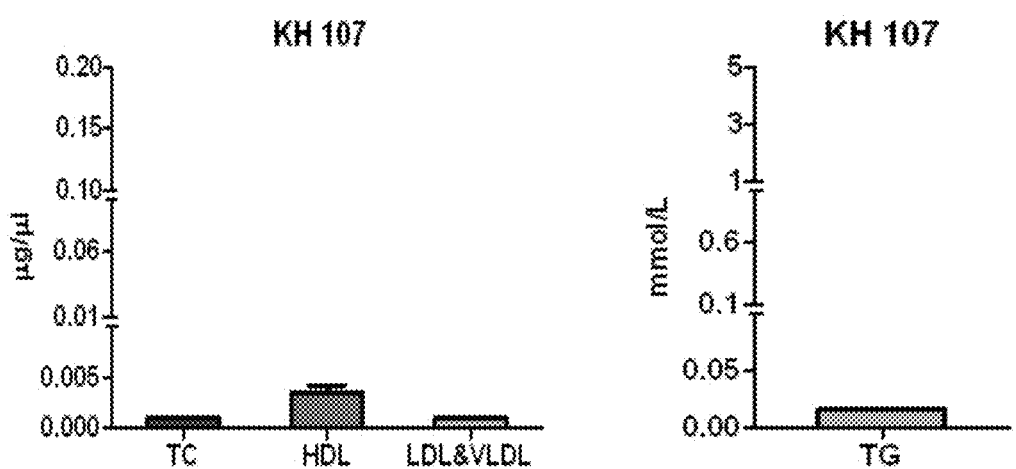
FIG. 9 shows the quantification of TC, HDL, LDL/VLDL and TG of sample KH 107.

Quantification of TC, HDL, LDL/VLDL and TG of sample KH 107 (FIG. 9)

| Sample | TC (µg/µl) | HDL (µg/µl) | LDL/VLDL (µg/µl) | TG (mmol/L) |
|---|---|---|---|---|
| KH 107 | 0.001 ± 0.000 | 0.003 ± 0.000 | 0.001 ± 0.000 | 0.017 ± 0.001 |

TABLE 12

Figure 10:
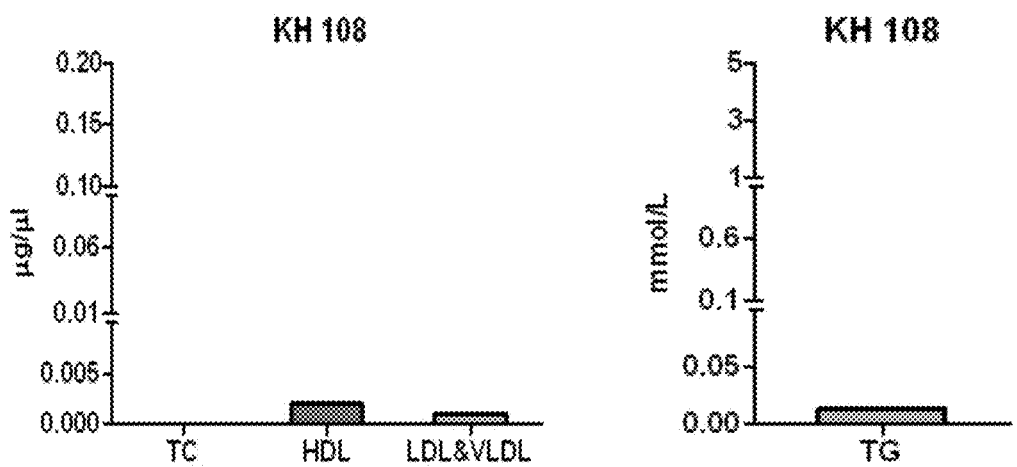
FIG. 10 shows the quantification of TC, HDL, LDL/VLDL and TG of sample KH 108.

Quantification of TC, HDL, LDL/VLDL and TG of sample KH 108 (FIG. 10)

| Sample | TC (µg/µl) | HDL (µg/µl) | LDL/VLDL (µg/µl) | TG (mmol/L) |
|---|---|---|---|---|
| KH 108 | 0.000 ± 0.000 | 0.002 ± 0.000 | 0.001 ± 0.000 | 0.014 ± 0.000 |

TABLE 13

Figure 11:
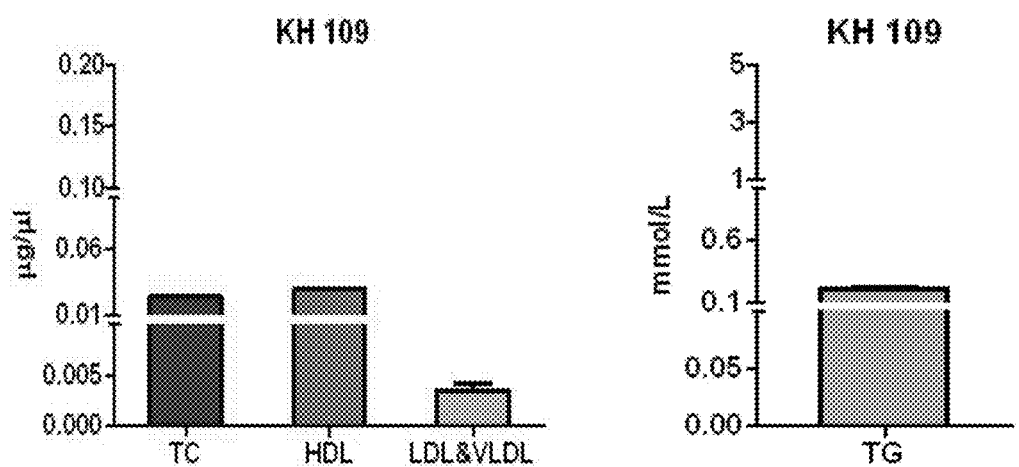
FIG. 11 shows the quantification of TC, HDL, LDL/VLDL and TG of sample KH 109 White wine.

Quantification of TC, HDL, LDL/VLDL and TG of sample KH 109 (FIG. 11)

| Sample | TC (µg/µl) | HDL (µg/µl) | LDL/VLDL (µg/µl) | TG (mmol/L) |
|---|---|---|---|---|
| KH 109 | 0.025 ± 0.001 | 0.03 ± 0.000 | 0.004 ± 0.000 | 0.207 ± 0.012 |

TABLE 14

Figure 12:
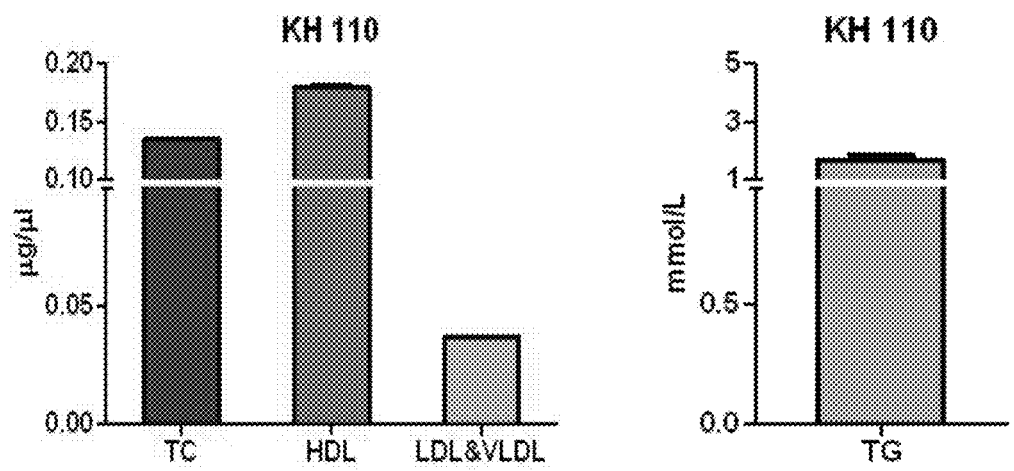
FIG. 12 shows the quantification of TC, HDL, LDL/VLDL and TG of sample KH 110 Red wine.

Quantification of TC, HDL, LDL/VLDL and TG of sample KH 110 (FIG. 12)

| Sample | TC (µg/µl) | HDL (µg/µl) | LDL/VLDL (µg/µl) | TG (mmol/L) |
|---|---|---|---|---|
| KH 110 | 0.134 ± 0.001 | 0.18 ± 0.001 | 0.037 ± 0.000 | 1.684 ± 0.154 |

TABLE 15

Figure 13:
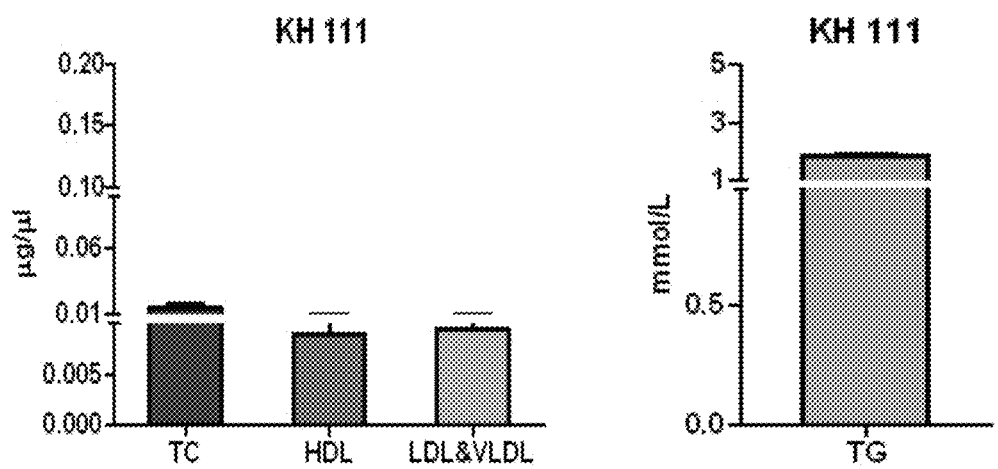
FIG. 13 shows the quantification of TC, HDL, LDL/VLDL and TG of sample KH 111 Young Soy Edamame.

Quantification of TC, HDL, LDL/VLDL and TG of sample KH 111 (FIG. 13)

| Sample | TC (µg/µl) | HDL (µg/µl) | LDL/VLDL (µg/µl) | TG (mmol/L) |
|---|---|---|---|---|
| KH 111 | 0.015 ± 0.003 | 0.009 ± 0.001 | 0.01 ± 0.001 | 1.865 ± 0.028 |

TABLE 16

Figure 14:
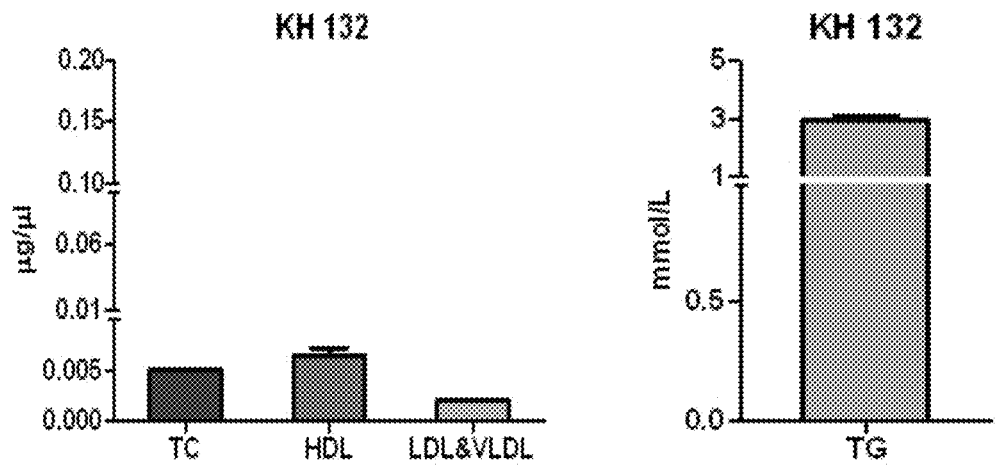
FIG. 14 shows the quantification of TC, HDL, LDL/VLDL and TG of sample KH 132 Red hot pepper.

Quantification of TC, HDL, LDL/VLDL and TG of sample KH 132 (FIG. 14)

| Sample | TC (µg/µl) | HDL (µg/µl) | LDL/VLDL (µg/µl) | TG (mmol/L) |
|---|---|---|---|---|
| KH 132 | 0.005 ± 0.000 | 0.007 ± 0.001 | 0.002 ± 0.000 | 2.928 ± 0.161 |

In Vitro Study 2—Lipid Panel

Figure 15:
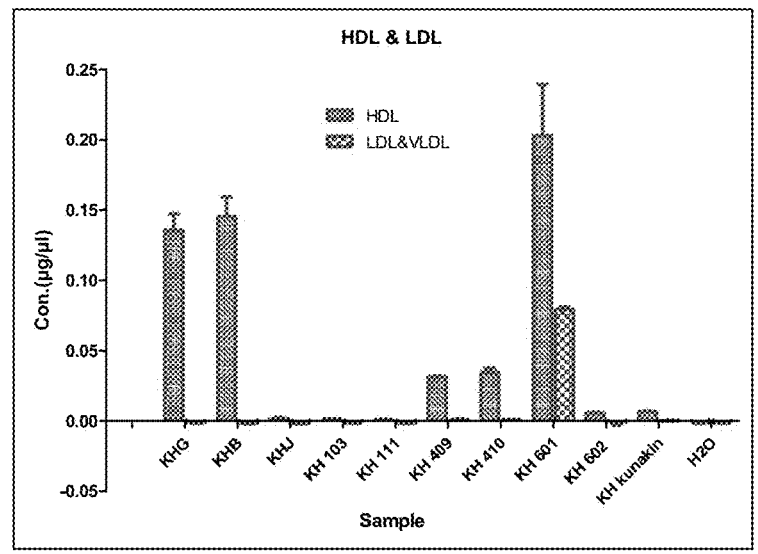
FIG. 15 shows the HDL and LDL of KH Green and KH Blue.
Figure 16:
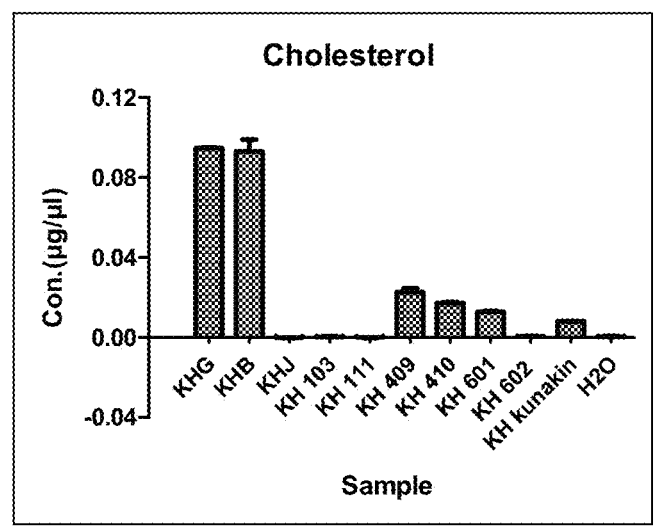
FIG. 16 shows the Cholesterol in KH Green and KH Blue.
Figure 17:
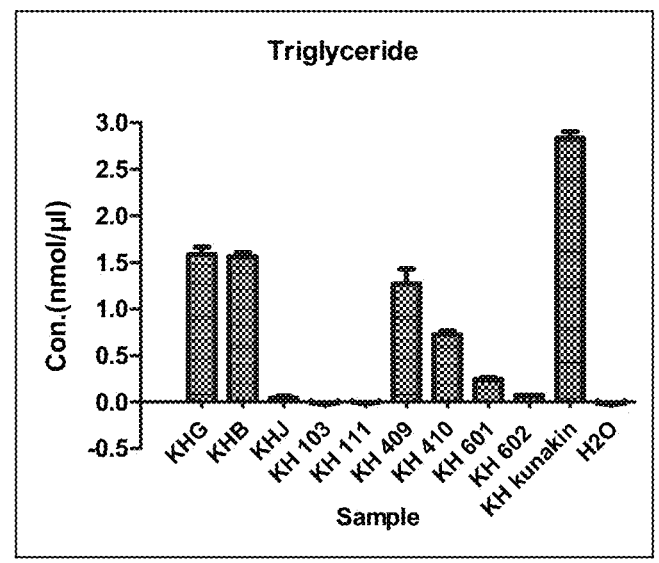
FIG. 17 shows the Tryglicerid in KH Green and KH Blue.
Figure 18:
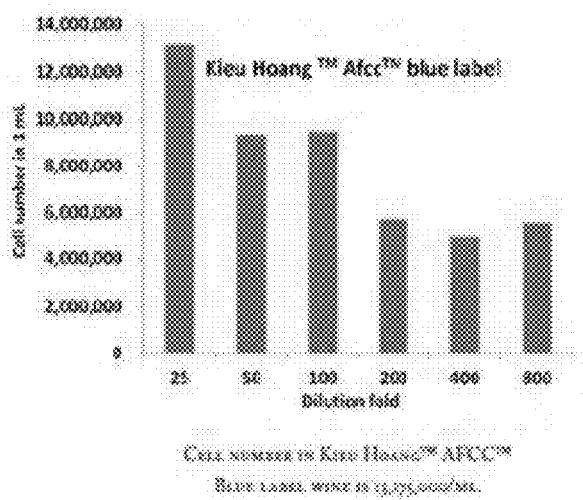
FIG. 18 shows the cell count on KIEU HOANG™ Blue label is 13,175,000/mL.
Figure 19:
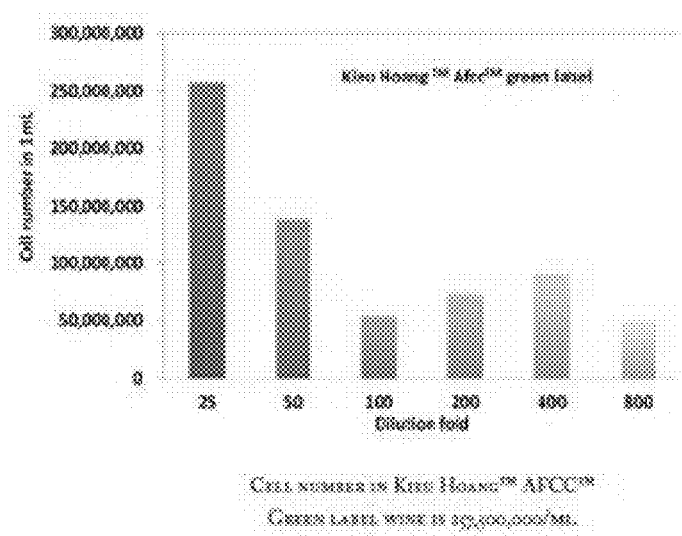
FIG. 19 shows the cell count on KIEU HOANG™ Green label is 257,500,000/mL.
Figure 20:
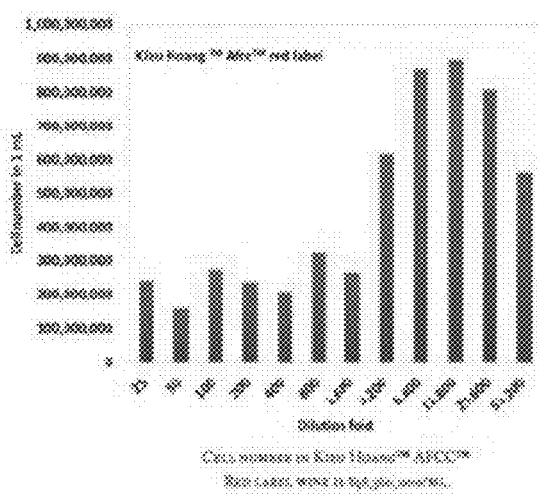
FIG. 20 shows the cell count on KIEU HOANG™ Red label is 898,560,000/mL.
Figure 21:
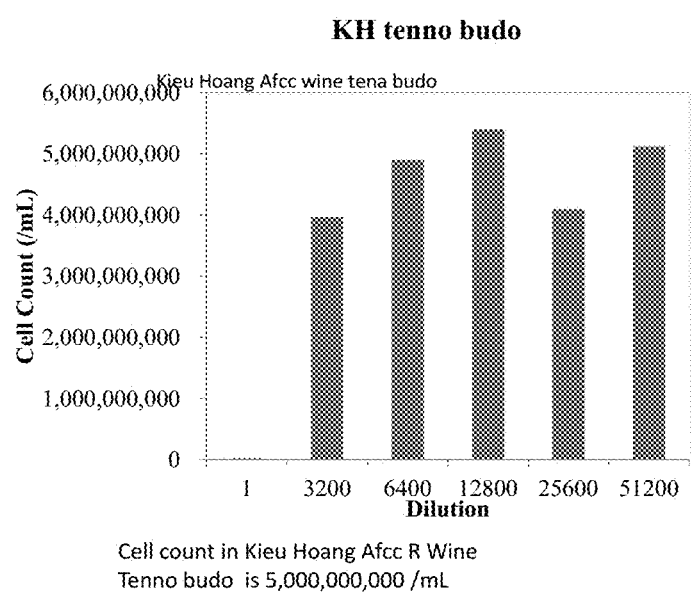
FIG. 21 shows the cell count on KIEU HOANG™ Tennobudo is 5,000,000,000/mL.
Figure 25:
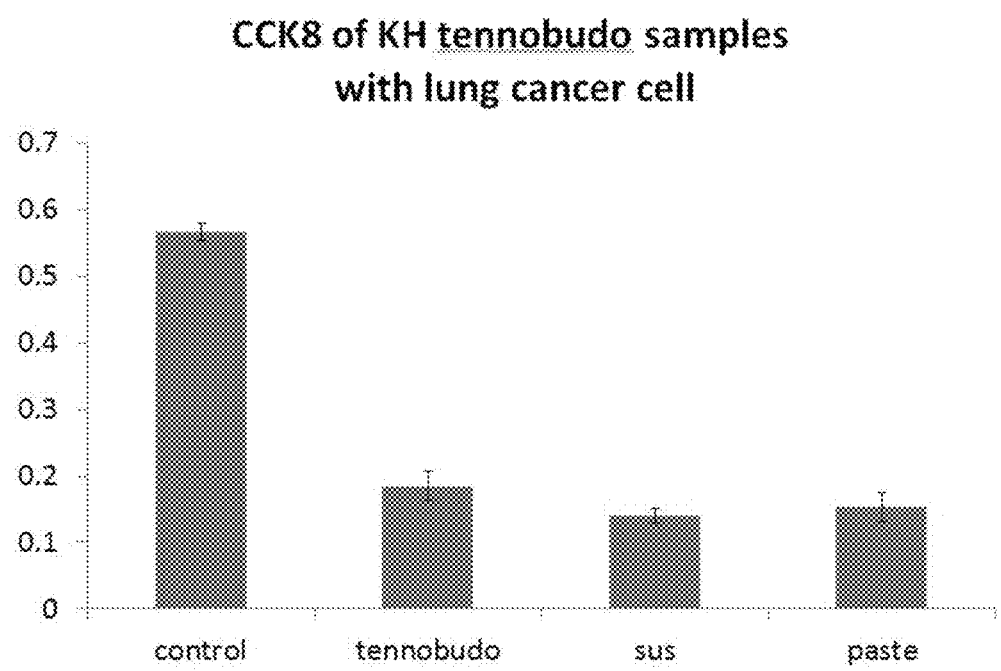
FIG. 25 shows the inhibition of KIEU HOANG™ Tennobudo label in lung cancer.
Figure 26:
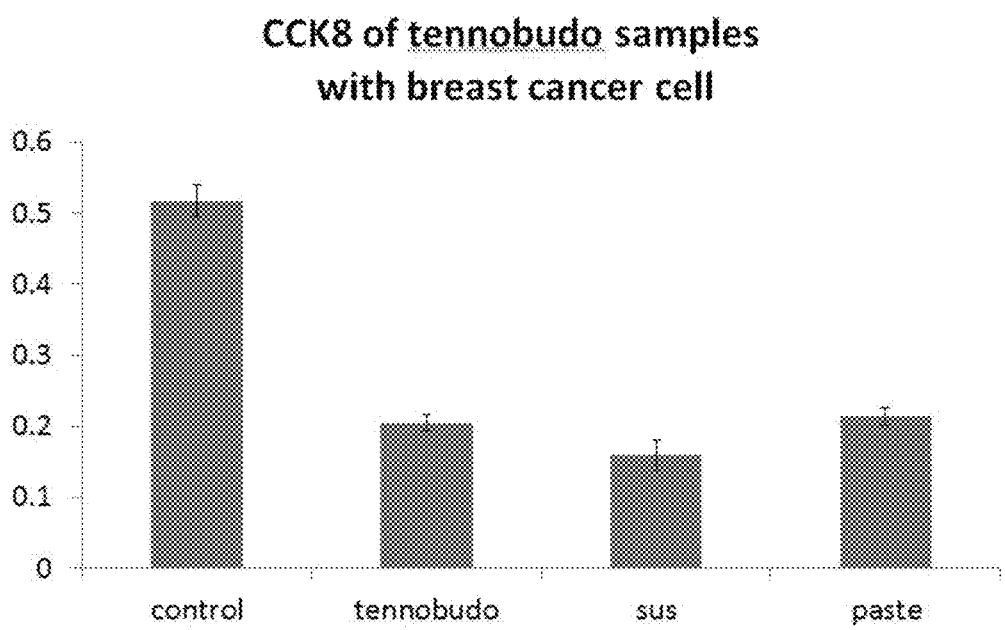
FIG. 26 shows the inhibition of KIEU HOANG™ Tennobudo label in breast cancer.
Figure 28:
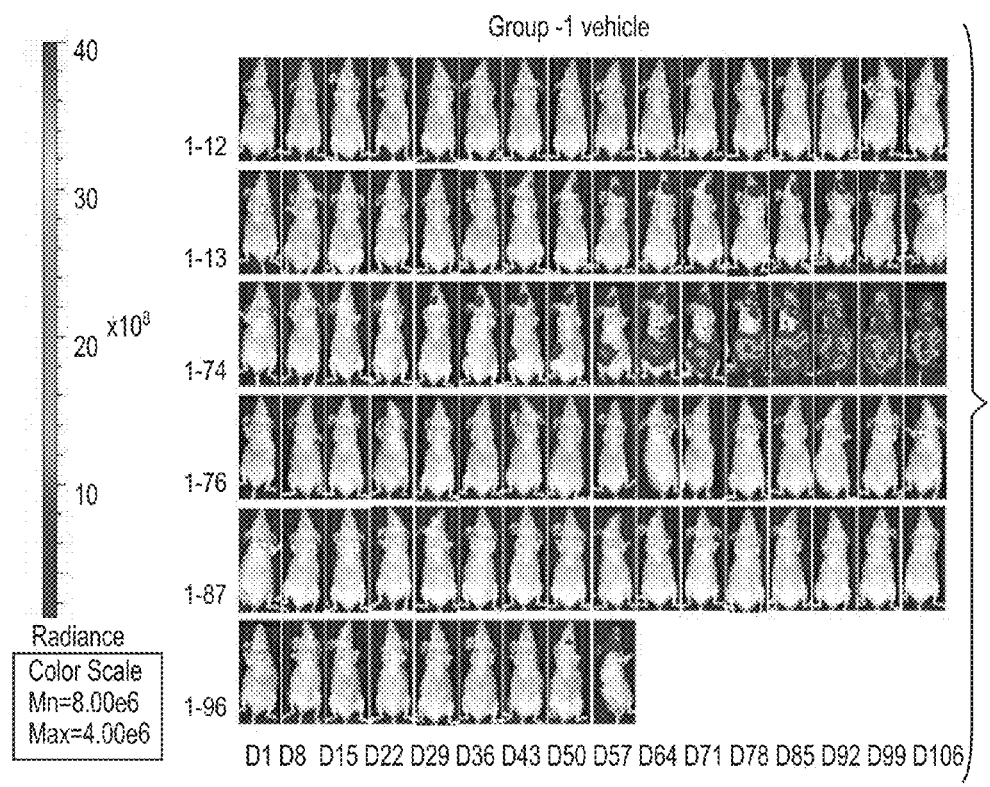
FIG. 28 shows the Leukemia cancer signal in mice, group 1 (Vehicle).
Figure 29:
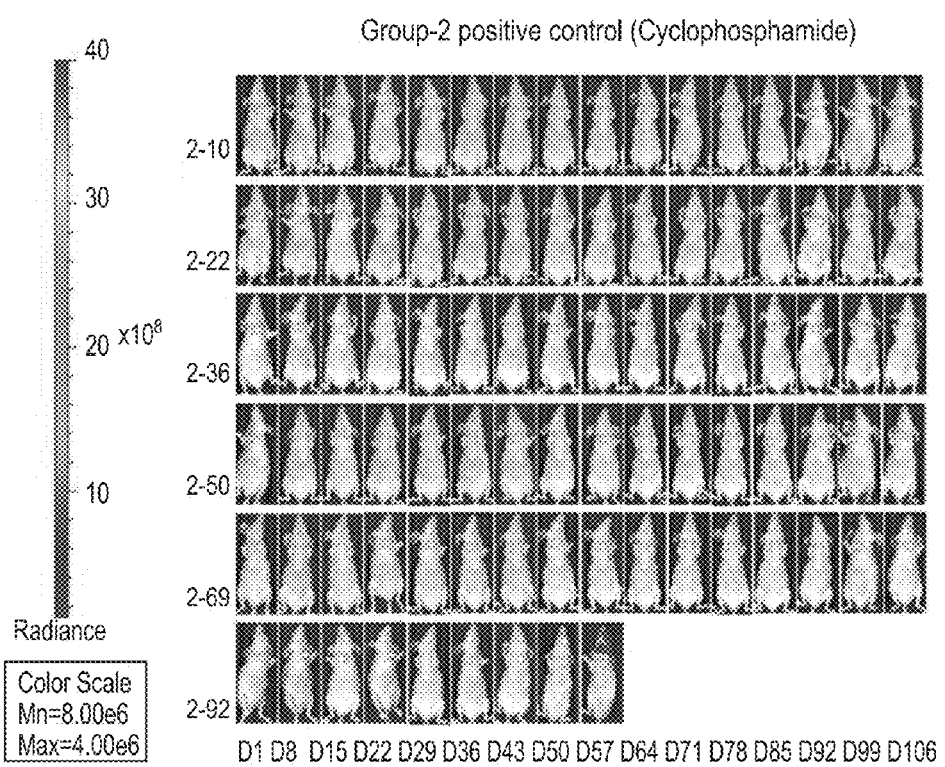
FIG. 29 shows the Leukemia cancer signal in mice, group 2 (Positive control).
Figure 30:
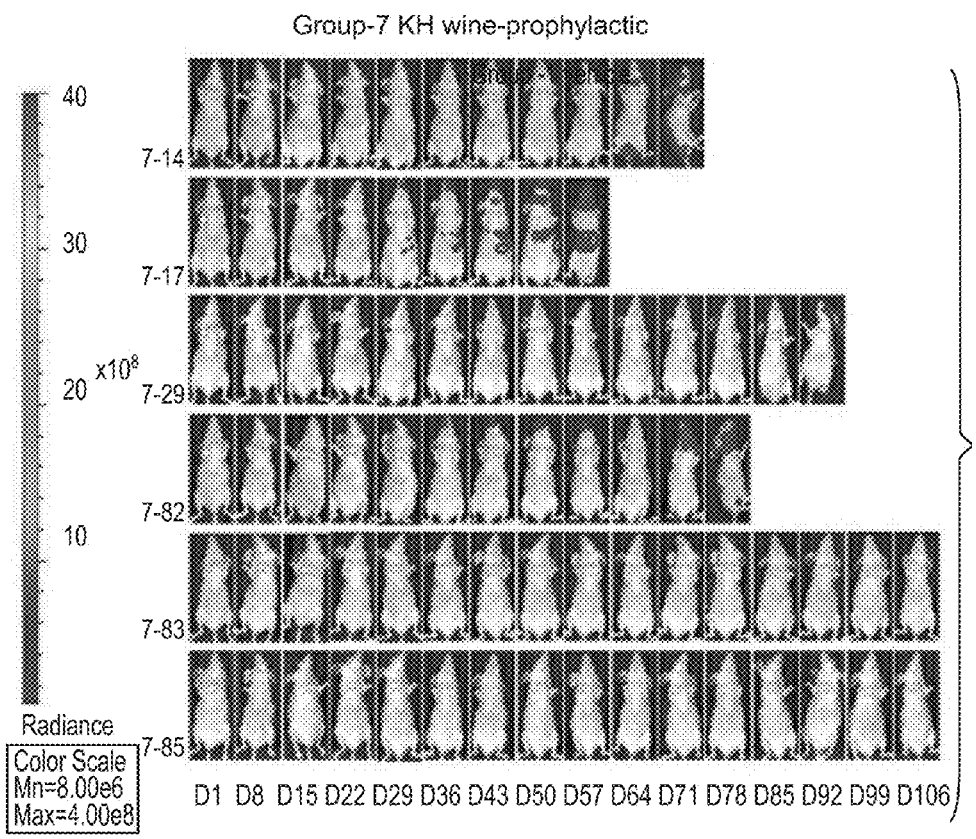
FIG. 30 shows the Leukemia cancer signal in mice, group 7 (Prophylactic).
Figure 31:
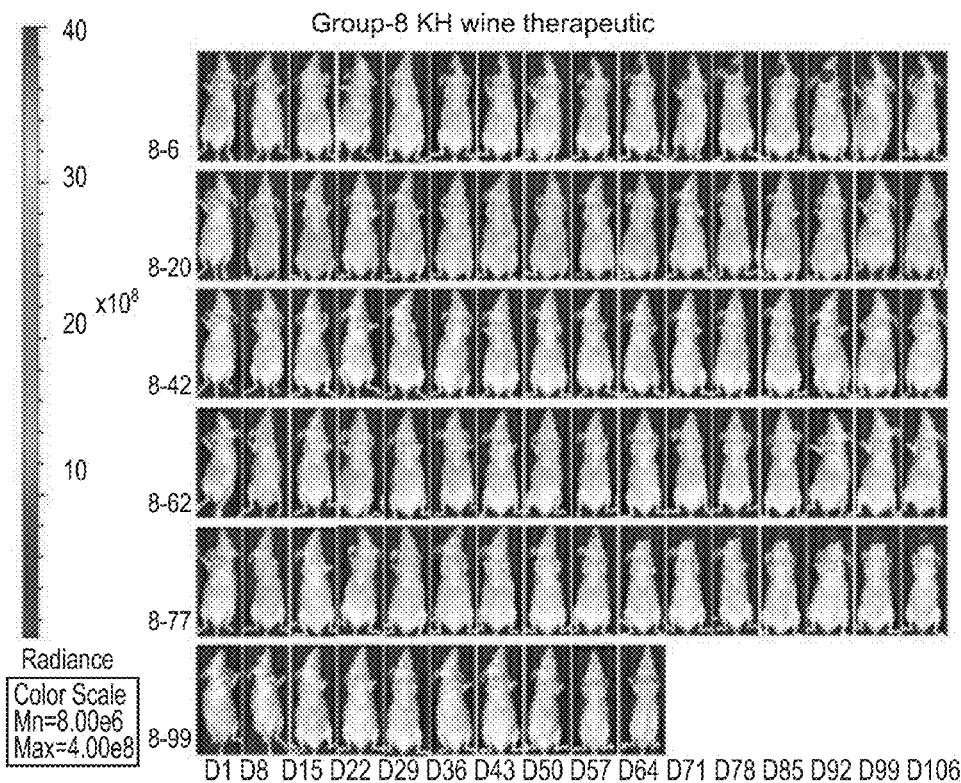
FIG. 31 shows the Leukemia cancer signal in mice, group 8 (Therapeutic).

The second lipid panel was performed on the KIEU HOANG™ Blue Label Wine as well as the Green Label Wine by Wuxi Pharma, one of the top ten CRO labs in the world. It was found that the levels of HDL are also very high (FIGS. 15-17).

In Vitro Study 3—Living Cells in Wine

The living cells are also found in all KIEU HOANG™ wine, from the low level of less than one million cells per mL, up to five billion cells per mL (FIGS. 18-21). Another finding shows that the taste of wine will be better with the higher concentration of cells. A number of studies also show the higher concentration of cells, the better efficacy.

In Vitro Study 4—Lung and Breast Cancer

It was found in the in vitro study of the four different labels of KIEU HOANG™ wine that the wine can inhibit the growth of the cancer cells, especially the lung and breast cancers (FIGS. 22-26).

In Vitro Study 5—KIEU HOANG™ Wine Green Label Wine and Diabetics

An in vitro study was performed by Wuxi Pharma, one of the ten largest CRO labs in the world. The study demonstrated that KIEU HOANG™ Green Label with the cell count of 257,500,000 mL can help in glucose uptake, which means that after drinking wine, diabetic patients have a lower sugar level in their systems (FIG. 27).

The higher the number of cells, the lower the sugar level is, the mechanism being due to KH good healthy living cells found in KIEU HOANG™ wine. Wine formulations containing KH wine good healthy cells in which the RNA synthesizes good proteins send signals to the damaged, sick, and bad cells that trigger synthesis of good proteins to transform the cells to become good healthy cells. Further, signals are sent to the other currently undamaged cells to synthesize good proteins to protect them from being damage, infection, and from being prone to DNA and other cellular alterations. Signals are sent to the patient's body to produce new cells that are healthy and to forbid them from being affected by intra- and extracellular damaging signals.

In Vivo Study 1: Leukemia Cancer Vs KIEU HOANG Wine Red Label

The in vivo study was also conducted at Wuxi Pharma. The study found that KIEU HOANG wine Red label helped to slow the growth of the cancer to compare with the vehicle control (FIGS. 28-31).

Volunteer Study 1—Lipid Panel

Since 1985, the volunteer's cardiologist prescribed Lipitor® but the volunteer never took the prescribed drug. Instead, the volunteer started running for two hours, exercising every day since 1983.

In Jan. 28, 2013, the volunteer performed a health checkup. The triglyceride level was 1,114 mg/dL, the cholesterol level was 346 mg/d, the HDL level was 44 mg/dL, LDL levels were beyond an upper limit (>400 mg/dL), and high blood pressure was found. The volunteer refused to take the drug Lipitor and also the drug to lower blood pressure. Instead, he turned to KIEU HOANG™ wine in which he discovered that KIEU HOANG™ wine had the highest levels of High Density Lipoprotein. Therefore, the volunteer believed that KIEU HOANG™ wine would help in lowering the cholesterol, triglyceride, and LDL levels. The results were confirmed.

In June 2013, after the volunteer's cholesterol test at Rui Jin Hospital, his doctor concluded that triglyceride, hypertension, and cholesterol levels were still high, but his doctor did not know how high his levels were in Jan. 28, 2013 test.

During the period from Jan. 28, 2013 until Jun. 3, 2013, the volunteer drank two glasses of KIEU HOANG™ Blue, Green, Red, or Gold label per night. Triglyceride levels dropped from 1,114 mg/dL down to 379 mg/dL. Cholesterol dropped from 346 mg/dL down to 235 mg/dL. HDL levels increased from 44 mg/dL up to 48 mg/dL. LDL dropped down from beyond the up limit >400 mg/dL to 125 mg/dL, as described in the charts below.

|  | Jan. 1, 2013 | Jun. 3, 2013 |
| --- | --- | --- |
| Triglyceride | 1114 mg/dL | 379 mg/dL |
| Cholesterol | 346 mg/dL | 235 mg/dL |
| HDL | 44 mg/dL | 49 mg/dL |
| LDL | beyond up limit (>400 mg/dL) | 125 mg/dL |

On Aug. 6, 2013, the volunteer's family physician looked at the results from the Rui Jin Hospital and prescribed some medicines which contained chemicals to decrease cholesterol and triglyceride levels. Instead of taking the medications, the volunteer continued drinking KIEU HOANG™ wines and in addition began to take 2 capsules of KUNAKIN™ (359 proteins in soy), 2 capsules of KUNAMIN™ (grape concentrate with seed, flesh, stem, and skin), and 4 capsules of KHCARE™ CardioTrim® Men's Formula, along with an hour of fast walking on treadmill while practicing a healthy diet.

On Sep. 10, 2013, a test was performed again after the change of regiment of Aug. 6, 2013. The results showed a decrease of triglyceride levels from 1,114 mg/dL down to 101 mg/dL. Cholesterol levels went down from 346 mg/dL to 235 mg/dL. HDL increased from 44 mg/dL to 50 mg/dL. LDL went from beyond an upper limit of >400 mg/dL to 158 mg/dL. Triglyceride levels decreased 1,102.9%. Cholesterol levels decreased 140%. HDL increased 110%. LDL decreased 253%, as described in the charts below.

|  | Jan. 1, 2013 | Jun. 3, 2013 | Sept. 10, 2013 | Increase (%) |
| --- | --- | --- | --- | --- |
| Triglyceride | 1114 mg/dL | 379 mg/dL | 101 mg/dL | −1102.9% |
| Cholesterol | 346 mg/dL | 235 mg/dL | 235 mg/dL | −140% |
| HDL | 44 mg/dL | 49 mg/dL | 60 mg/dL | 110% |
| LDL | beyond up limit (>400 mg/dL) | 125 mg/dL | 158 mg/dL | −253% (based on 400 mg/dL) |

Volunteer Study 2—Lower Sugar Levels in Diabetics

The measurement of sugar level of a particular volunteer was performed in mid-November and mid December 2014. In mid-November three volunteers consumed one bottle of KIEU HOANG™ wine Red label. After dinner the particular volunteer measured his sugar level, which showed a reading of 7.0. In mid-December the same three volunteers consumed a bottled of Tennobuddo (former Guilliams), and after dinner the particular volunteer measured his sugar level, which showed a reading of 6.9. The sugar reading level was performed twice to prove it. For the particular volunteer, even if he administered the prescribed chemical drug, his lowest sugar level was typically 11.5-12 mmol/L.

As such, KIEU HOANG™ wine Green Label™, Red Label™, Yellow Label™, Purple Label™, and/or Tenno-Budo™ (former Guilliams) with the cell contents between 275,000,000/cells per ml up to 5,000,000,000 (5 billion) living cells per ml, will help to lower sugar level in diabetics down to 7 and 6.9 mmol/L from 11.5-12 mmol/L after dinner.

Figure 32:
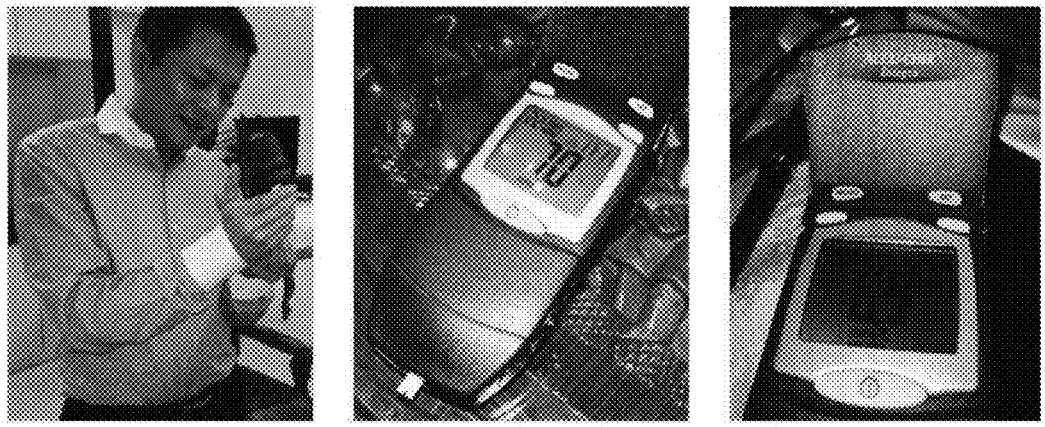
FIG. 32 shows the inventor's business partner testing his blood sugar levels after drinking KIEU HOANG™ Red label and Tennobudo wines.

It was found that the higher the number of cells, the better for not only lowering down sugar level in diabetics, but also for the taste of the wine. FIG. 32 shows a volunteer testing his blood sugar levels after drinking KIEU HOANG™ Red label and Tennobudo wines.

Volunteer Study 3—the Inventor's Living Moving Cells Vice Versa Living Cells in KIEU HOANG Wine Cells from plants, animals, and humans are the same and live forever. For example, even after a cancer patient dies, the bad cancer cells are still alive. The wine grape has been used to make wine through crushing, and at different temperatures, bacteria and virus can be eliminated at a low pH of 3.5-4.0. However, the living cells are still present in the wine.

The cells from the inventor (A), from KH103 (B) and from Porcine TB (C) are show in FIG. 39A-C for comparison. In order to prove cells are still alive in the human component, the skin under the feet of the inventor was removed from the body, ground into powder, centrifuged at high speed, and underwent high temperature of heating up to 120° C. After the aforementioned steps, the cells were still alive. The cells consist of two rings called double ring. The outer ring is DNA and the inner ring is RNA.

Figure 33:
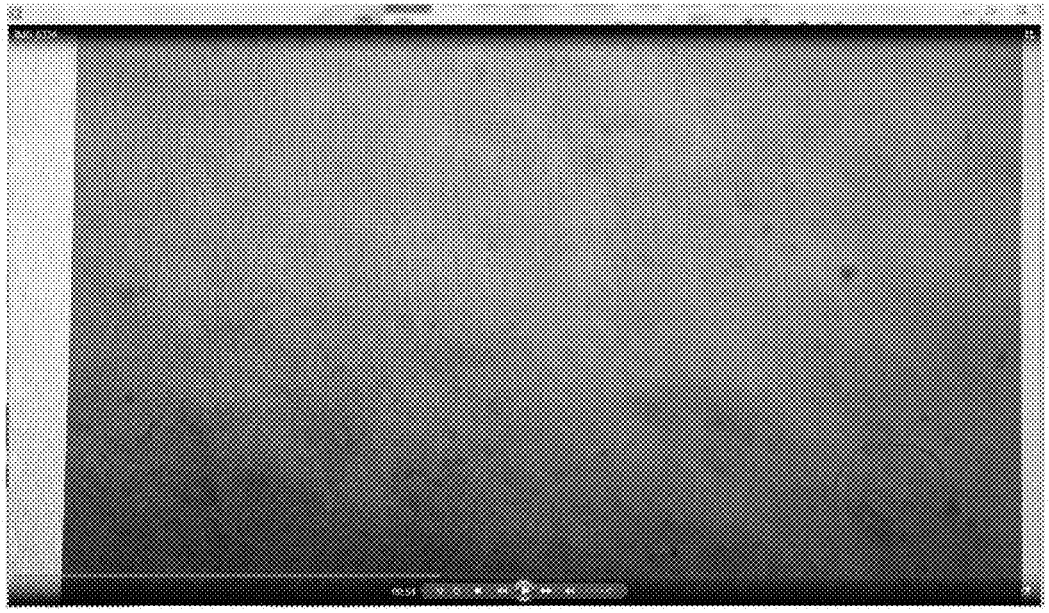
FIG. 33 shows the human moving cells in the inventor's feet. Still pictures from video to prove the cells are moving are taken from 00:54 seconds into the video.
Figure 34:
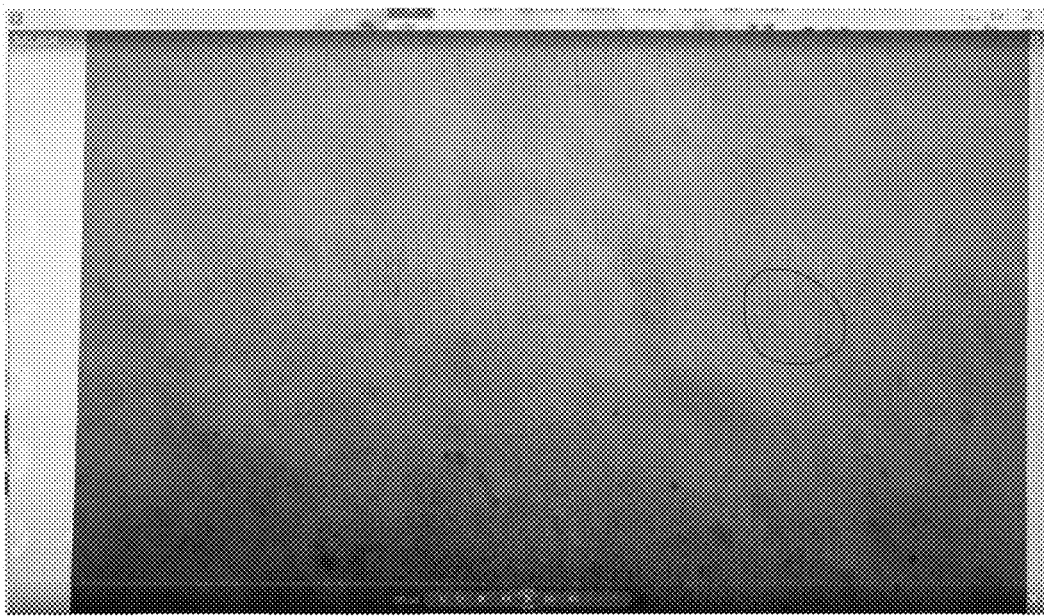
FIG. 34 shows the human moving cells in the inventor's feet. Still pictures from video to prove the cells are moving are taken from 00:59 seconds into the video.
Figure 35:
FIG. 35 shows the human moving cells in the inventor's feet. Still pictures from video to prove the cells are moving are taken from 01:06 seconds into the video.

FIG. 33 shows human moving cells in the inventor's feet. Still pictures were taken from video to prove the cells are moving from 00:54 seconds into the video. FIG. 34 shows human moving cells in the inventor's feet. Still pictures were taken from video to prove the cells are moving from 00:59 seconds into the video. FIG. 35 shows human moving cells in the inventor's feet. Still pictures were taken from video to prove the cells are moving from 01:06 seconds into the video.

Figure 36:
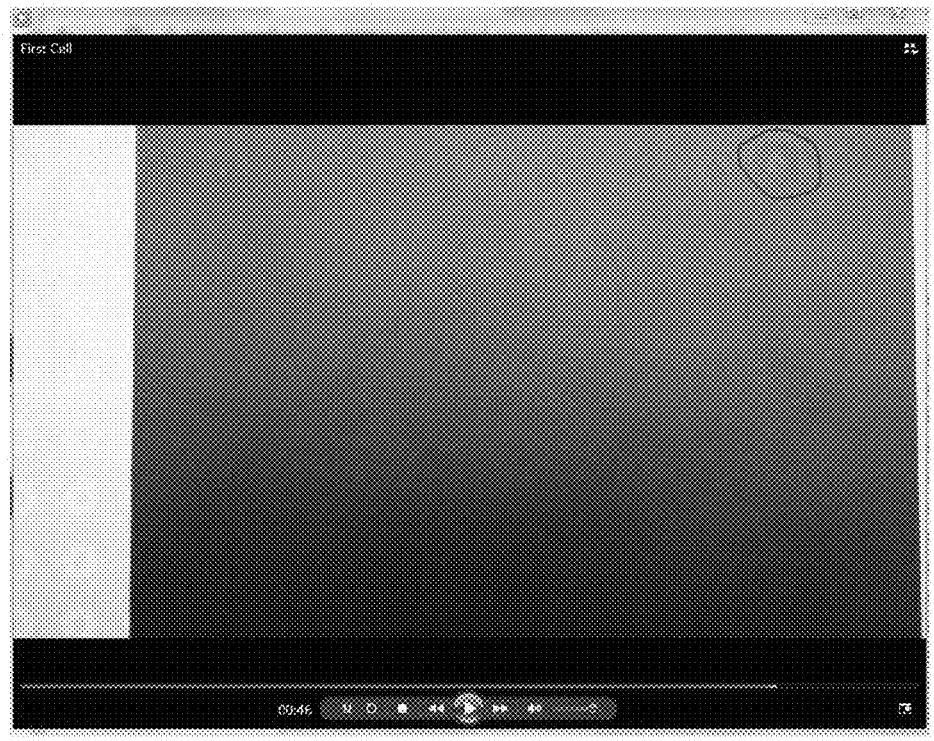
FIG. 36 shows the moving cells of the plant in KIEU HOANG™ wine. Still pictures from video to prove the cells are moving are taken from 00:46 seconds into the video.
Figure 37:
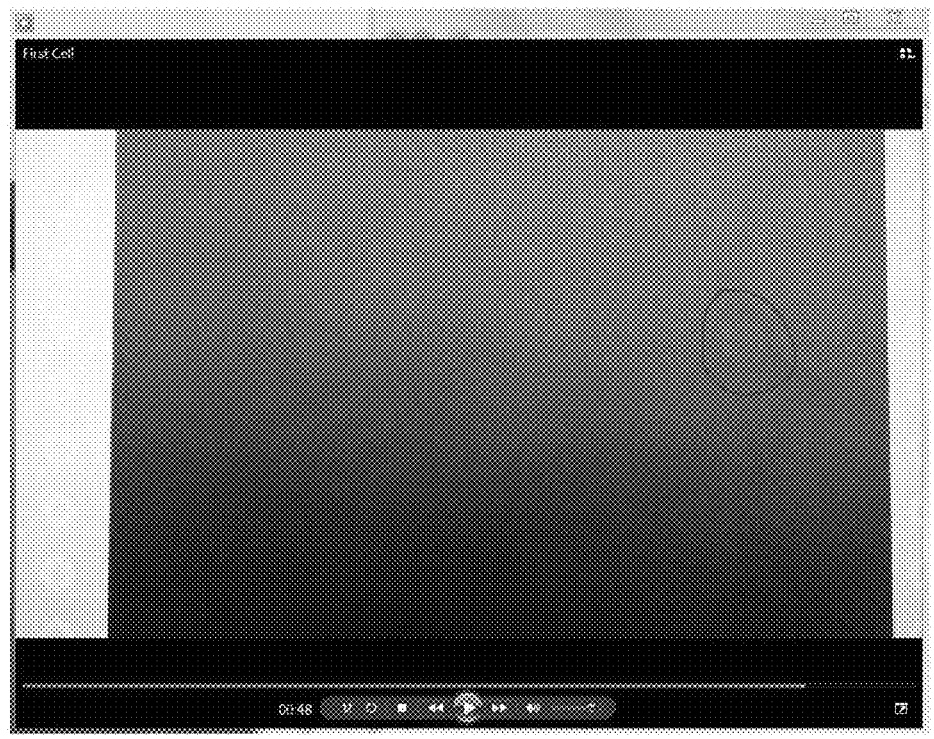
FIG. 37 shows the moving cells of the plant in KIEU HOANG™ wine. Still pictures from video to prove the cells are moving are taken from 00:48 seconds into the video.
Figure 38:
FIG. 38 shows the moving cells of the plant in KIEU HOANG™ wine. Still pictures from video to prove the cells are moving are taken from 00:50 seconds into the video.

FIG. 36 shows the moving cells of the plant in KIEU HOANG™ wine. Still pictures were taken from video to prove the cells are moving from 00:46 seconds into the video. FIG. 37 shows the moving cells of the plant in KIEU HOANG™ wine. Still pictures were taken from video to prove the cells are moving from 00:48 seconds into the video. FIG. 38 shows the moving cells of the plant in KIEU HOANG™ wine. Still pictures were taken from video to prove the cells are moving from 00:50 seconds into the video.

In Vitro Study 6—KH601 Grape Seed Extract and KH602 Resveratrol

An in vitro study of KH601 and KH602 was also performed by Wuxi Pharma. The study showed that KH601 and KH602 contain high density lipoprotein (APOA-1) but are low in cholesterol and triglyceride.

In Vivo Study 2—KH609 Grape Seed Extract and KH610 Resveratrol

In this study of KH609 and KH610 vs Leukemia cancer, it was found that KH609 and KH610 have helped to slow the growth of the Leukemia cancer cells.

In Vitro Study 7—Testing by SDS Page and Cell Count of KUNAMIN™

Figure 41:
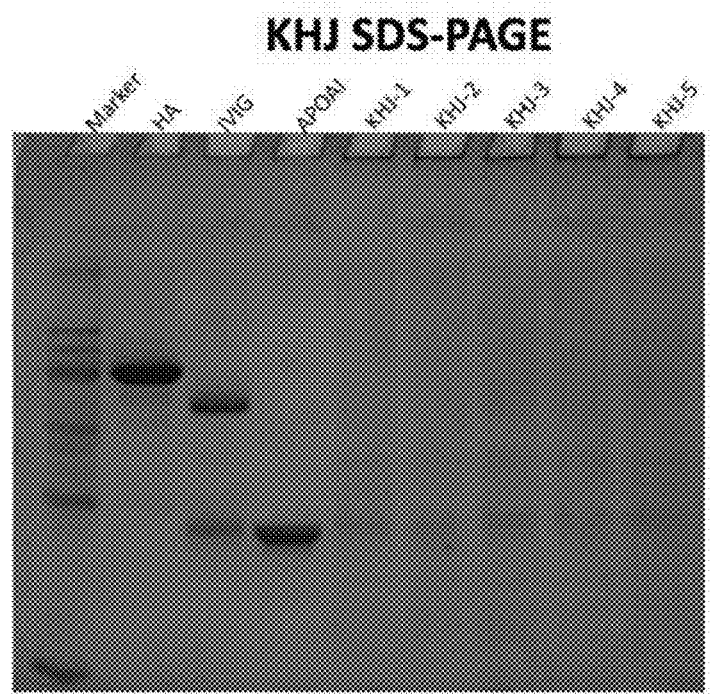
FIG. 41 shows an image of the KHJ SDS-Page, particularly the band of molecular weight of KHJ-1, KHJ-2, KHJ-3, KHJ-4 and KHJ-5 at different dilutions similar to that of immunoglobulin and High density lipoprotein (APOA-1) of the human plasma.

KHJ, KH601, and KH602 are the code names of KUNAMIN™. SDS Page was performed to examine the molecular weight of KUNAMIN™. It was found that the molecular weight of KUNAMIN™ is similar to that of immunoglobulin and APOA1 (High Density Lipoprotein) found in human plasma (FIG. 41).

Figure 42:
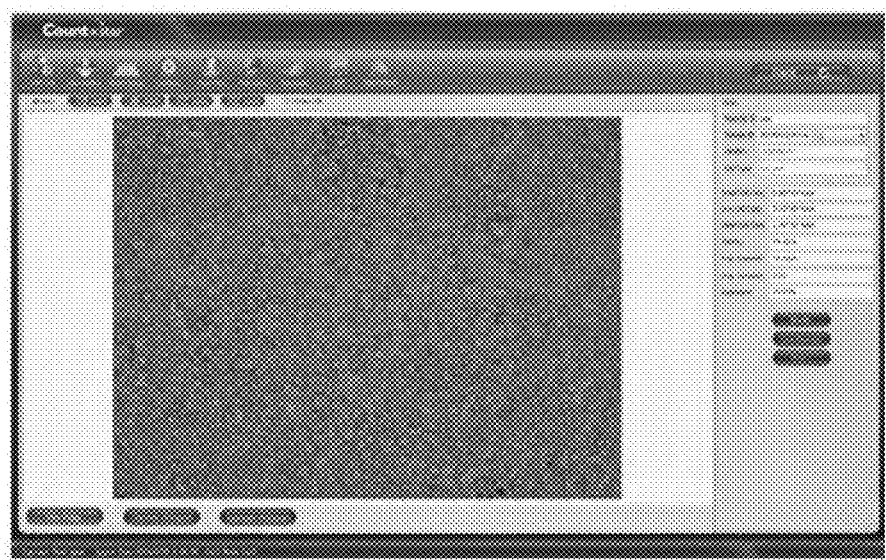
FIG. 42 shows an image of the cell count of KUNAMIN™.

KUNAMIN™ contains between cells from 10,000,000 cells per ml up to one billion cells count per ml in various concentration of KUNAMIN™ (FIG. 42).

In Vitro Study 8—Testing of HDL/VLDL/LDL and Triglyceride in KUNAMIN™

The study was performed at Wuxi Pharma to detect level of High Density Lipoprotein (HDL), LDL (Low Density Lipoprotein), and Very Low Density Lipoprotein (VLDL). KH601, one of the components in KUNAKIN™, has a very high level of High Density Lipoprotein (HDL), which is good cholesterol. KHJ and KH 601 have the lowest levels of LDL, VLDL, and triglyceride.

Glucose Uptake in KUNAMIN™

Glucose metabolism is a primary source of energy and biomaterials for the maintenance of cell homeostasis. Extra glucose is stored in the muscles and liver as glycogen which is hydrolyzed to glucose and released into the blood when needed. The rate of glucose uptake in cells is dynamic and tightly regulated by hormones and/or growth factors including insulin.

GLUT4 is the insulin-regulated glucose transporter found in adipose tissues and striated muscle (skeletal and cardiac) that is responsible for insulin-regulated glucose transport into the cell. Under conditions of low insulin, GLUT4 is sequestered in intracellular vesicles in muscle and fat cells. Insulin induces a rapid increase in the uptake of glucose by inducing the translocation of GLUT4 from these vesicles to the plasma membrane. As the vesicles fuse with the plasma membrane, GLUT4 transporters are inserted and become available for transporting glucose, and glucose absorption increases.

This study is using 2-deoxy-D-[$^3$H]-glucose to track the effect of testing proteins on the rate of glucose uptake in 3T3-L1 cells in responsive to insulin.

Materials and Reagents
Reagents:
HEPES, Invitrogen (Cat#15630130)
MgSO4, SIGMA (Cat#63138)
CaCl2, FLUKA (Cat#06991)
KCl, SIGMA (Cat#P9333)
NaCl, Fisher (Cat#BMA51202)
BSA, Gibco (Cat# A6003)
Deoxy-D-glucose, 2-[1, 2-3H (N)], Perkin Elmer (Cat#NET328A250UC)
Insulin, Sigma (Cat#I2643)
2-DEOXY-D-GLUCOSE, Sigma (Cat#D6134)
FBS, Invitrogen (Cat#10100147)
DMEM, Invitrogen (Cat#11965118)
Dexamethasone, Sigma (Cat#D1756-25MG)
3-Isobutyl-1-methylxanthine, IBMX, Sigma (Cat#15879)
Apparatus and Plates:
Top Seal-A sealing film, Perkin Elmer (Cat#6005250)
Tri-Carb, (Perkin Elmer)
96 Well Microplates (Nunc-442587)
96-well micro titer black clear plate (Greiner-655090)
Cell:
3T3-L1 fibroblasts cell (Cell bank of Chinese academy of sciences-Cat No. GNM25)
Testing Samples:
10 testing proteins were provided by RAAS US as shown in Table 17:

TABLE 17

| Testing Samples | Volume/Quality |
|---|---|
| KHG | 10 ml |
| KHB | 10 ml |
| KHJ | 10 ml |
| KH 103 | 10 ml |
| KH 111 | 10 ml |
| KH 409 | Powder |
| KH 410 | Powder |
| KH 601 | Powder |
| KH 602 | Powder |
| KH Kunakin | Powder |

Experimental Procedure

Dissolve the powder samples at 20 g: 100 ml ddH$_2$O. Filter the solid particles from the solution. Filter all the rest samples at the same time.

3T3-L1 fibroblasts were cultured in culture medium I (DMEM containing 25 mM glucose, 1% PS, 10% FBS) at 37° C. with 5% CO2.

3T3-L1 fibroblasts were differentiated into adipocytes 2 days post confluent with culture medium II (DMEM, 10% FBS, 1% PS) containing 1 ug/ml insulin, 1 uM dexamethasone, and 0.5 mM IBMX (day 0). Media were replaced with culture medium II containing 1 ug/ml insulin and culture 2 days. (day 2). Media is changed to 10% FBS/DMEM (day 4). Feed cells with 10% FBS/DMEM every two days. Full differentiation is usually achieved by day 8.

Seed 200 ul/well 2×10$^5$/ml 3T3-L1 adipocytes to 96 wells cell culture plate (culture medium II containing 1 ug/ml insulin), culture overnight at 37° C. with 5% CO2. 3T3-L1 adipocytes were incubated in serum free medium for starvation overnight. 3T3-L1 adipocytes were washed with KRPH buffer (5 mM Na2HPO4, 20 mM HEPES, pH 7.4, 1 mM MgSO4.1 mM CaCl2, 136 mM NaCl, 4.7 mM KCl, and 1% BSA) three times. Add 90 ul KRPH containing 100 nM human insulin/vehicle and incubate for 30 min at 37° C. and 5% CO2. Add 10 ul KRPH containing 0.25 uCi 1-[$^3$H]-2-deoxyglucose/well and 50 umol/l 2-deoxyglucose and Incubate 10 min in 95% air/5% CO2 at 37° C. The transport was stopped by rinsing the cells with cold PBS containing 10 mM glucose for three times. The adipocytes were lysed in 50 ul 10% KOH for 5 min. Then the aliquots were subjected to scintillation counting using TriCap. Note: cell differentiation is necessary from 3T3-L1 fibroblasts to 3T3-L1 adipocytes.

Results

Figure 43:
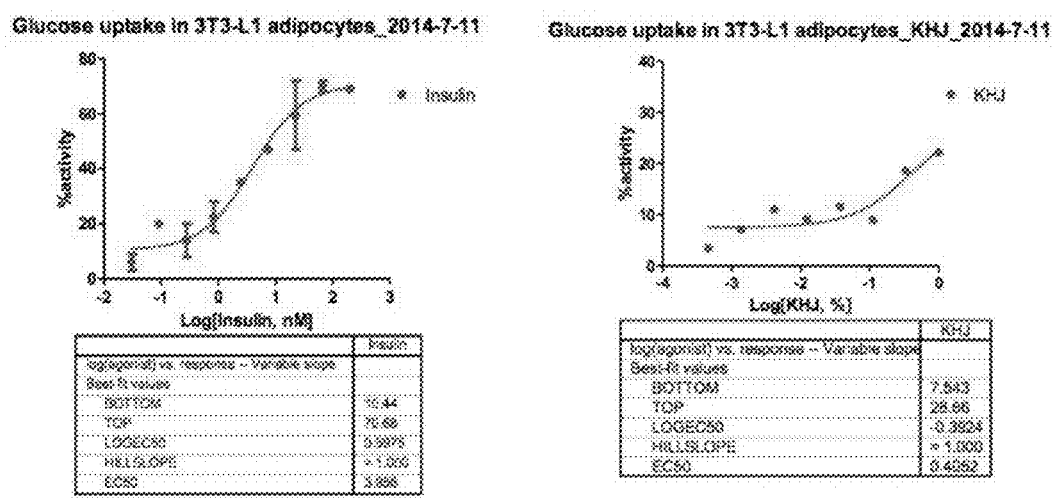
FIG. 43 shows a graph depicting how KUNAMIN™ helps to generate Insulin for Glucose uptake in DIABETICS.

Ten testing proteins were tested in eight concentrations (the starting concentration is 1%, 3 folds dilution) using 3T3-L1 adipocytes in glucose uptake assay (FIGS. 43-45). The assay was conducted twice independently. If the obtained EC50 values from two repeats were not in the 3-fold range of difference, the assay was repeated one more time. Data were analyzed use GraphPad Prism 5:

| Insulin | | | | KHG | | | | KHB | | | |
|---|---|---|---|---|---|---|---|---|---|---|---|
| Dose (nM) | Count | | % Activity | Dose | Count | | % Activity | Dose | Count | | % Activity |
| 200 | 980 | 989 | 68% | 70% | 1.00000% | 726 | 769 | 12.1% | 21.6% | 1.00000% | 672 | 702 | 0.3% | 6.9% |
| 66.67 | 979 | 1000 | 68% | 72% | 0.33333% | 816 | 726 | 31.9% | 12.1% | 0.33333% | 770 | 763 | 21.8% | 20.2% |
| 22.22 | 887 | 1000 | 47% | 72% | 0.11111% | 772 | 764 | 22.2% | 20.5% | 0.11111% | 712 | 733 | 9.1% | 13.7% |
| 7.41 | 884 | 992 | 47% | 70% | 0.03704% | 720 | 667 | 10.8% | −0.8% | 0.03704% | 722 | 779 | 11.2% | 23.8% |
| 2.47 | 736 | 828 | 14% | 35% | 0.01235% | 692 | 622 | 4.7% | −10.7% | 0.01235% | 636 | 638 | −7.6% | 7.2% |
| 0.82 | 800 | 746 | 28% | 17% | 0.00412% | 657 | 646 | −3.0% | −5.4% | 0.00412% | 689 | 734 | 4.0% | 13.9% |
| 0.27 | 709 | 761 | 8% | 20% | 0.00137% | 725 | 710 | 11.9% | 8.6% | 0.00137% | 763 | 723 | 20.2% | 11.5% |
| 0.09 | 760 | 587 | 20% | −18% | 0.00046% | 783 | 466 | 24.6% | −44.9% | 0.00046% | 801 | 749 | 28.6% | 17.2% |

| KHJ | | | | KH 103 | | | | | |
|---|---|---|---|---|---|---|---|---|---|
| Dose | Count | | % Activity | Dose | Count | | % Activity | Control | Average |
| 1.00000% | 772 | 696 | 22.2% | 5.5% | 1.00000% | 696 | 702 | 5.5% | 6.9% | 1078 | 1127 |
| 0.33333% | 777 | 734 | 23.3% | 13.9% | 0.33333% | 793 | 801 | 26.8% | 28.6% | 1048 | |
| 0.11111% | 720 | 703 | 10.8% | 7.1% | 0.11111% | 704 | 730 | 7.3% | 13.0% | 1101 | |
| 0.03704% | 724 | 723 | 11.7% | 11.5% | 0.03704% | 724 | 771 | 11.7% | 22.0% | 1279 | |
| 0.01235% | 727 | 698 | 12.3% | 6.0% | 0.01235% | 621 | 708 | −10.9% | 8.2% | 699 | 671 |
| 0.00412% | 721 | 785 | 11.0% | 25.1% | 0.00412% | 724 | 733 | 11.7% | 13.7% | 596 | |
| 0.00137% | 743 | 664 | 15.9% | −1.5% | 0.00137% | 730 | 679 | 13.0% | 1.8% | 696 | |
| 0.00046% | 742 | 631 | 15.6% | −8.7% | 0.00046% | 691 | 723 | 4.4% | 11.5% | 692 | |

Dose response curve fits: GLUCOSE UPTAKE in KUNAMIN™.

CONCLUSION

For insulin reference, get the EC50 5 times.

| Insulin EC50 (nM) | 2014/7/11 | 2014/7/14 | 2014/8/27 | 2014/8/28 | 2014/8/29 |
|---|---|---|---|---|---|
| | 3.958 | 2.464 | 2.535 | 6.944 | 6.66 |

The sample KHG, KGJ and KH602 were tested twice on 3T3-L1 adipocytes glucose uptake assay. They all have activity on 3T3-L1 adipocytes glucose uptake. The results we obtained two times were consistent.

| EC50 | KHG | KHJ | KH 602 |
|---|---|---|---|
| n = 1 | 0.036% | 0.405% | 0.449% |
| n = 2 | 0.014% | 0.828% | 0.199% |

The sample KH409, KH410 and KH601 were tested twice on 3T3-L1 adipocytes glucose uptake assay. They have inhibition effect on 3T3-L1 adipocytes glucose uptake. The results obtained two times were consistent.

| IC50 | KH 409 | KH 410 | KH 601 |
|---|---|---|---|
| n = 1 | 0.192% | 0.250% | 1.481% |
| n = 2 | 0.161% | 0.728% | 0.488% |

The sample KHB, KH103, KH111 and KH Kunakin were tested twice on 3T3-L1 adipocytes glucose uptake assay. They all have no activity on 3T3-L1 adipocytes glucose uptake assay. The results obtained two times were consistent.

In Vivo Study 3

The Molt-4-luc leukemia model was used to evaluate the anti-cancer efficacy of different compounds in Balb/c nude mice. On day 50 after the cell implantation, the median relative bioluminescence of vehicle group was 153.43 and the positive control group was 1.40; while the KHJ prophylactic group and KHJ therapeutic group produced relative bioluminescence of 2.84 and 1.32, respectively. On day 111 after the cell injection, two mice died and three mice showed bioluminescence signal in vehicle control group. In the positive control group, one mouse died which showed bioluminescence signal. However, in KHJ treatment groups, all mice were alive, and one mouse in the prophylactic group and one mouse in the therapeutic group exhibited bioluminescence signal in this molt-4-luc leukemia model. In summary, the results showed that the test compound of KHJ was well-tolerated by the tumor-bearing mice and the testing article KHJ had inhibition on tumor growth.

The objective was to evaluate the anti-tumor efficacy of different compounds in leukemia model in Balb/c nude mice. All the experiments were conducted in the AAALAC-accredited animal facility in compliance with the protocol approved by the Institutional Animal Care and Use Committee (IACUC).

Experimental Preparations

Female Balb/c nude mice, with a body weight of approximately 20 grams, were obtained from an approved vendor (Shanghai BK Laboratory Animal Co., LTD., Shanghai, China). Upon arrival, animals were assessed as to their general health by a member of a veterinary staff or authorized personnel. Animals were acclimated for at least three days (upon arrival at the experiment room) before being used for the study. Animals were housed in groups during acclimation and individually housed during in-life. The animal room environment was adjusted to the following target conditions: temperature 20-25° C., relative humidity 40-70%, 12 hours of artificial light, and 12 hours dark. Temperature and relative humidity were monitored daily.

All animals had access to Certified Rodent Diet ad libitum. Animals were not fasted prior to the study. Water was autoclaved before provided to the animals ad libitum. Periodic analyses of the water were performed and the results were archived at WuXi AppTec. There were no known contaminants in the diet or water which, at the levels detected expected to interfere with the purpose, conduct or outcome of the study.

Cell Culture

The Molt-4-luc (Vendor link: Caliper-125057) tumor cells were maintained in vitro as a suspension culture in RPMI 1640 medium supplemented with 10% fetal bovine serum at 37° C. in an atmosphere of 5% CO2 in air. The tumor cells were routinely subcultured twice weekly. The cells growing in an exponential growth phase were harvested and counted for tumor inoculation.

The testing articles (KH51, KHJ, KHR, KH103, KH111, KH606, KH610, KHJ2, KHJ3, KHJC and KH103C) were provided by RAAS. Cyclophosphamide (Shanxi Powerdone Pharmaceutical CO. LTD.; Lot. #04120503) was formulated in saline.

Experimental Protocol

Mice were randomly assigned to 16 groups (vehicle control, positive control, and 14 testing article groups) based on the body weight. Mice in the prophylactic group were administered with testing articles four weeks before tumor implantation according to Table 13. Mice in the vehicle, the positive control, and the therapeutic groups were administered with testing articles right after cell injection according to Table 18. Whole body and metastatic bioluminescence were measured and recorded.

TABLE 18

Experimental Design

| Group | Treatment | Dosage and dosing volume | Dosing Route | Dosing Schedule | Animal Number |
|---|---|---|---|---|---|
| 1 | Vehicle | — | Free to drink | — | 6 |
| 2 | Positive control: Cyclophosphamide | 100 mpk for the first dose, 75 mpk for the following doses. | IP | BIW | 6 |
| 3 | KH51 (Prophylactic group*) | 20 ml/kg | IP | QD | 6 |
| 4 | KH51 (Therapeutic group**) | 20 ml/kg | IP | QD | 6 |
| 5 | KHJ (Prophylactic group*) | — | Free to drink | — | 6 |
| 6 | KHJ (Therapeutic group**) | — | Free to drink | — | 6 |
| 7 | KHR (Prophylactic group*) | — | Free to drink | 24 h on (D0-D38)$^a$ 8 h on 16 h off (D39-D44)$^a$ 16 h on 8 h off (D45-end)$^a$ | 6 |
| 8 | KHR (Therapeutic group**) | — | Free to drink | 24 h on (D28-38)$^a$ 8 h on 16 h off (D39-D44)$^a$ 16 h on 8 h off (D45-end)$^a$ | 6 |
| 9 | KH103 (Prophylactic group*) | — | Free to drink | — | 6 |
| 10 | KH103 (Therapeutic group**) | — | Free to drink | — | 6 |
| 11 | KH111 (Prophylactic group*) | — | Free to drink | — | 6 |
| 12 | KH111 (Therapeutic group**) | — | Free to drink | — | 6 |
| 13 | KH609 (Prophylactic group*) | — | Free to drink | — | 6 |
| 14 | KH609 (Therapeutic group**) | — | Free to drink | — | 6 |
| 15 | KH610 (Prophylactic group*) | — | Free to drink | — | 6 |
| 16 | KH610 (Therapeutic group**) | — | Free to drink | — | 6 |

Note:
*Prophylactic group: six mice, free access to drink the test sample, the test sample was given four weeks before cell injection.
**Therapeutic group: six mice, free access to drink the test sample, the test sample was given right after cell injection.
Vehicle, positive control groups: treatment was given right after cell injection.

TABLE 19

The treatment of animals with signal

Treatment of mice with signal[b]

| Group | D46-D51[a] | D52[a] | D53-D59[a] | D60-92[a] | D93-D111[a] |
|---|---|---|---|---|---|
| 1 Vehicle | Vehicle | Vehicle | Vehicle | Vehicle | Vehicle |
| 2 Positive control: Cyclophosphamide | Cyclophosphamide | Cyclophosphamide | Cyclophosphamide | Cyclophosphamide | Cyclophosphamide |
| 3 KH51 (Prophylactic group*) | KHJ | KHJ1 + KH51 | KHJ1 | KHJC | KHJ |
| 4 KH51 (Therapeutic group**) | KHJ | KHJ1 + KH51 | KHJ1 | KHJC | KHJ |
| 5 KHJ (Prophylactic group*) | KHJ | KHJ1 + KH51 | KHJ1 | KHJC | KHJC |
| 6 KHJ (Therapeutic group**) | KHJ | KHJ1 + KH51 | KHJ1 | KHJC | KHJC |
| 7 KHR (Prophylactic group*) | KHJ | KHJ1 + KH51 | KHJ1 | KH103C | KHJ |
| 8 KHR (Therapeutic group**) | KHJ | KHJ1 + KH51 | KHJ1 | KH103C | KHJ |
| 9 KH103 (Prophylactic group*) | KHJ | KHJ2 + KH51 | KHJ2 | KH103C | KHJ |
| 10 KH103 (Therapeutic group**) | KHJ | KHJ2 + KH51 | KHJ2 | KHJC + KH103C | KHJ |
| 11 KH111 (Prophylactic group*) | KHJ | KHJ2 + KH51 | KHJ2 | KHJC + KH103C | KHJC + KH103C |
| 12 KH111 (Therapeutic group**) | KHJ | KHJ2 + KH51 | KHJ2 | KHJC + KH103C | KHJ |
| 13 KH609 (Prophylactic group*) | KHJ | KHJ2 + KH51 | KHJ3 | KHJ3 | KHJ |
| 14 KH609 (Therapeutic group**) | KHJ | KHJ2 + KH51 | KHJ3 | KHJ3 | KHJ |
| 15 KH610 (Prophylactic group*) | KHJ | KHJ2 + KH51 | KHJ3 | KHJ3 | KHJ |
| 16 KH610 (Therapeutic group**) | KHJ | KHJ2 + KH51 | KHJ3 | KHJ3 | KHJ |

Note:
[a]Days after the cell injection
[b]The doses were changed during the experiment as requested by the sponsor.
*Prophylactic group: six mice, free access to drink the test sample, the test sample was given four weeks before cell injection.
**Therapeutic group: six mice, free access to drink the test sample, the test sample was given right after cell injection.
Vehicle, positive control groups: treatment was given right after cell injection.

Bioluminescence Measurements

The inoculated mice were weighted and intraperitoneally injected luciferin at 150 mg/kg. After 10 minutes of the luciferin administration, the animals were pre-anesthetized with the mixture gas of oxygen and isoflurane. When the animals were in a complete anesthetic state, they was moved them into the imaging chamber for bioluminescence measurements with IVIS (Lumina II). The bioluminescence of the whole animal body, including primary and metastatic tumors, was measured and images are recorded.

Drugs and Materials

The test compounds (KH51, KHJ, KHR, KH103, KH111, KH606, KH610, KHJ2, KHJ3, KHJC and KH103C) were provided by RAAS. Cyclophosphamide (ShanXi Powerdone Pharmaceutical CO. LTD.; Lot. #04120503).

Data Analysis: Median Relative Bioluminescence

Bioluminescence (BL) of the whole animal body, including primary and metastatic tumors, was measured and images were recorded using a fixed intensity scale. Relative bioluminescence (RBL) value was calculated with IVIS Lumina II software and the data was recorded. Tumor growth curve was plotted with median relative bioluminescence.

$$RBL = RBL_t/RBL_0, \text{ where}$$

$RBL_t$—RBL value at time t $RBL_0$—RBL value at starting time

Data Analysis: Survival Animals and Animals with Signal of Cancer

Animals were kept receiving bioluminescent measurement once a week until Day 111 after the cell injection. The bioluminescence of the whole animal body, including primary and metastatic tumors, was measured. The survival animals and animals with signal of cancer were recorded.

Results: Median Relative Bioluminescence in Different Groups

Figure 46:
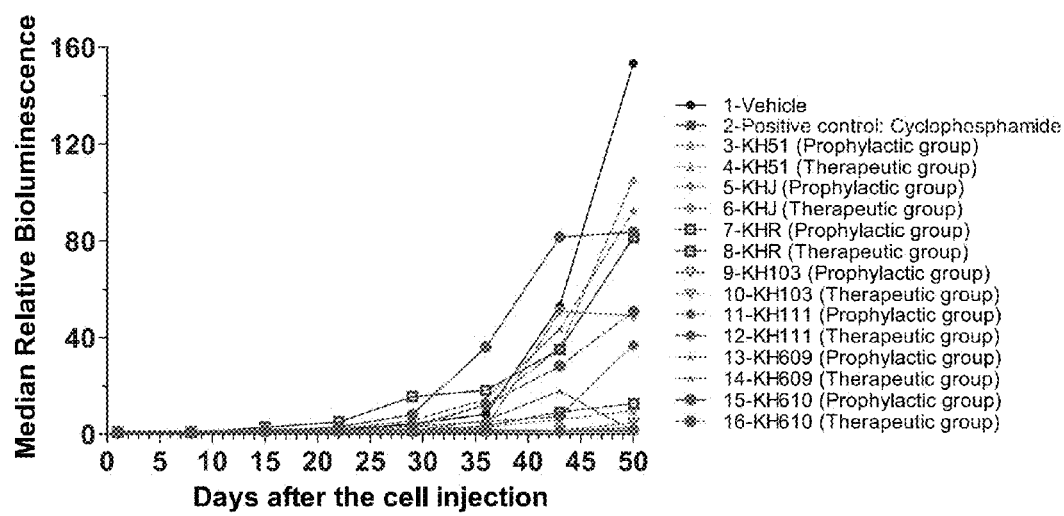
FIG. 46 shows a graph depicting median relative bioluminescence for the vehicle, positive control, and the other 14 items tested, including the KHJ609, KHJ610, and KHJ (the code names for KUNAMIN™). All the test items slowed down the growth of the Leukemia cancer cells and all are below the vehicle Median Relative Bioluminescence.

On day 50 after the cell implantation, the median relative bioluminescence of the vehicle group was 153.43 and the positive control group was 1.40. While the KHJ prophylactic group and KHJ therapeutic group produced relative bioluminescence of 2.84 and 1.32 respectively. The results showed that the testing article KHJ had inhibition on tumor growth. The median relative bioluminescence of different groups is shown in FIG. 46.

Results: Survival Animals and Animals with Signal of Cancer

Animals kept receiving bioluminescent measurement once a week until Day 111 after the cell injection. The bioluminescence of the whole animal body, including primary and metastatic tumors, was measured. The survival animals and animals with signs of cancer were recorded. On day 111 after the cell injection, two mice died and three mice showed bioluminescence signals in the vehicle control group. In the positive control group, one mouse died which showed bioluminescence signal. However, in the KHJ treatment groups, all mice were alive, and one mouse in prophylactic group and one mouse in therapeutic group exhibited bioluminescence signal in this Molt-4-luc leukemia model.

The survival animals and animals with signal of cancer were shown in Table 20.

TABLE 20

Summary on day 111 after the cell injection

| Group | Treatment | Animal Number | Animals # with bioluminescence signal | Survival animals # |
|---|---|---|---|---|
| 1 | Vehicle | 6 | 3 | 4 |
| 2 | Positive control: Cyclophosphamide | 6 | 1 | 5 |
| 3 | KH51 (Prophylactic group*) | 6 | 4 | 3 |
| 4 | KH51 (Therapeutic group**) | 6 | 3 | 5 |
| 5 | KHJ (Prophylactic group*) | 6 | 1 | 6 |
| 6 | KHJ (Therapeutic group**) | 6 | 1 | 6 |
| 7 | KHR (Prophylactic group*) | 6 | 4 | 2 |
| 8 | KHR (Therapeutic group**) | 6 | 2 | 5 |
| 9 | KH103 (Prophylactic group*) | 6 | 3 | 4 |
| 10 | KH103 (Therapeutic group**) | 6 | 1 | 5 |
| 11 | KH111 (Prophylactic group*) | 6 | 2 | 6 |
| 12 | KH111 (Therapeutic group**) | 6 | 2 | 4 |
| 13 | KH609 (Prophylactic group*) | 6 | 3 | 5 |
| 14 | KH609 (Therapeutic group**) | 6 | 4 | 4 |
| 15 | KH610 (Prophylactic group*) | 6 | 4 | 4 |
| 16 | KH610 (Therapeutic group**) | 6 | 4 | 4 |

Note:
*Prophylactic group: six mice, free access to drink the test sample, the test sample was given four weeks before the cell injection.
**Therapeutic group: six mice, free access to drink the test sample, the test sample was given right after the cell injection.
Vehicle, positive control groups: treatment was given right after the cell injection.

A molt-4-luc leukemia model was used to evaluate the anti-cancer efficacy of different compounds in Balb/c nude mice. On day 50 after the cell implantation, the median relative bioluminescence of the vehicle group was 153.43 and the positive control group was 1.40, while the KHJ prophylactic group and the KHJ therapeutic group produced relative bioluminescence of 2.84 and 1.32, respectively.

On day 111 after the cell injection, two mice died and 3 mice showed bioluminescence signal in the vehicle control group. In the positive control group, one mouse died which showed bioluminescence signal. However, in the KHJ treatment groups, all mice were alive, and one mouse in prophylactic group and one mouse in therapeutic group exhibited bioluminescence signal in this molt-4-luc leukemia model. The reasons for the death of the mice may be the tumor growth. Here, the mice which showed bioluminescence died. It means that the tumor growth is the dominant reason leading to the death of the mice. Note: one mouse (1/6) in KH609 prophylactic group died on day 44 after the cell injection. GraphPad Prism 5 was used for graph preparation.

The results showed that the testing article KHJ had inhibition on tumor growth. In the study of KH609 and KH610 vs Leukemia cancer, it was found that KH609 and KH610 helped to slow the growth of the Leukemia cancer cells.

Among the items tested, included were KHJ609, KHJ610, and KHJ, the code names for Kunamin™. As shown in FIG. 46, all the test items have slowed down the growth of the Leukemia cancer cells and all are below the vehicle Median Relative Bioluminescence.

Figure 47:
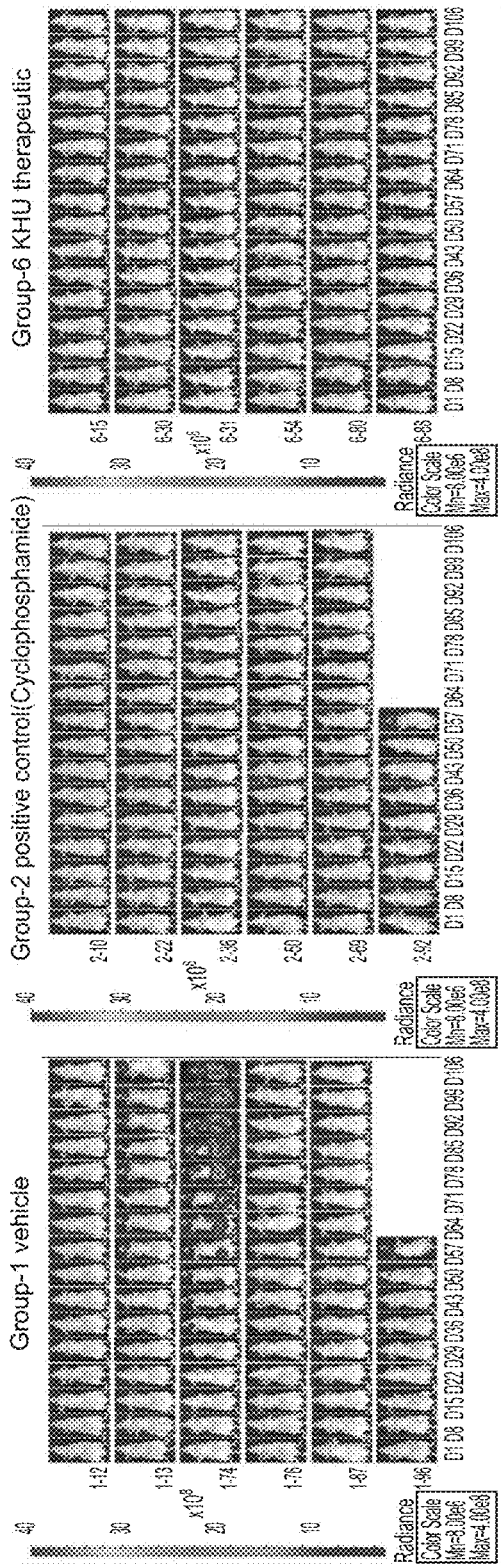
FIG. 47 shows images of bioluminescence of the KHJ Therapeutic group.

In the KHJ Therapeutic group (FIG. 47) none of the mice died until day 106, and none of them has shown a median relative bioluminescence in comparison with the vehicle group. Three of them have developed Leukemia and one died at day 57. Also to compare with the positive group, which used a drug, one mouse in the positive group died at day 57 as well. Due to the fact that the three mice in the vehicle did not grow the Leukemia, CRO has been requested to inject 20 million more Leukemia cells into those three mice in the vehicle, as well as all six mice in the KHJ until day 150. All mice in the vehicle group as well as the positive control group died. Mice in the KHJ group continued to live up to 280 days.

Figure 48:
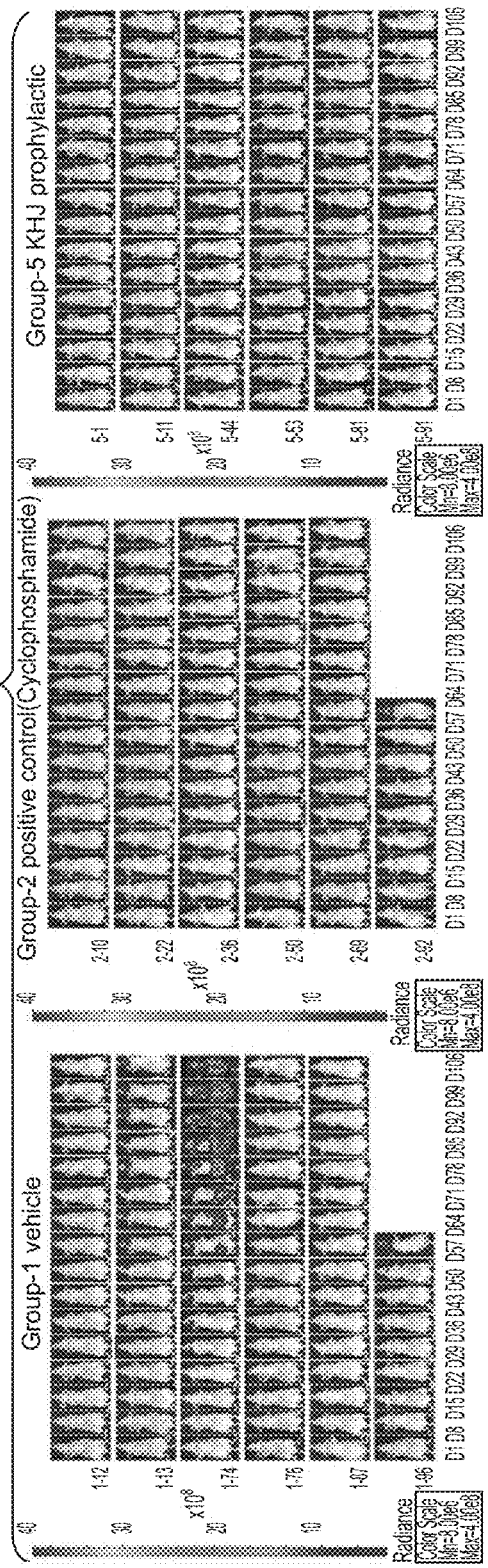
FIG. 48 shows images of bioluminescence of the KHJ Prophylactic group.

In the KHJ Prophylactic group (FIG. 48) none of the mice died until day 106. One mouse (5-53) showed a median relative bioluminescence, and the signal has become weaker thanks to the help of KHJ in converting Leukemia cancer cells into KH good healthy cells (from human, from plant and from animal). In comparison with the vehicle group, three mice developed Leukemia and one died at day 57. Also to compare with the positive group, which used a drug, one mouse in the positive group died at day 57 as well. Due to the fact that the three mice in the vehicle did not grow the Leukemia, the CRO was requested to inject 20 million more Leukemia cells into those three mice in the vehicle as well as all six mice in the KHJ in both groups (prophylactic and therapeutic) until day 150. All mice in the vehicle group as well as the positive control group died. Mice in the KHJ continued to live up to 300 days.

In conclusion, KUNAMIN™ has zero percent concentration of the juice. With higher concentration, more cells will be generated and it will be more efficacious in preventing and treating leukemia.

With the information contained herein, various departures from precise descriptions of the present subject matter will be readily apparent to those skilled in the art to which the present subject matter pertains, without departing from the spirit and the scope of the below claims. The present subject matter is not considered limited in scope to the procedures, properties, or components defined, since the preferred embodiments and other descriptions are intended only to be illustrative of particular aspects of the presently provided subject matter. Indeed, various modifications of the described modes for carrying out the present subject matter which are obvious to those skilled in chemistry, biochemistry, or related fields are intended to be within the scope of the following claims.

I claim:

1. A method of treating diabetes in a human in need thereof consisting essentially of administering a therapeutically effective amount of a mixture of grape seed and grape stem which has been crushed together and spray dried, to a human in need thereof to effectively treat the diabetes in the human.

2. The method of treating diabetes in a human of claim 1, wherein the spray drying of the mixture transforms the mixture into a powder for consumption by the human.

3. The method of treating diabetes in a human of claim 1, wherein the crushed mixture further includes ground flesh of and skin of the grape.

4. The method of treating diabetes in a human of claim 1, wherein the crushed mixture further includes wine added to the mixture.

5. The method of treating diabetes in a human of claim 4, wherein the wine has been aged in a temperature range of 15-20 C and is filtered and extracted prior to the wine being added to the mixture.

6. The method of treating diabetes in a human of claim 4, wherein the wine has 500,000 to 6 billion cells per milliliter of wine.

7. The method of treating diabetes in a human of claim 4, wherein the wine comprises APOA1 from protein of the wine.

8. The method of treating diabetes in a human of claim 1, wherein the crushed mixture is crushed in a grinder in a temperature range of 20-30 C and a pH of the mixture after crushing is in the pH range of 3.4-8.0.

* * * * *